US011724998B2

(12) United States Patent
Mani et al.

(10) Patent No.: US 11,724,998 B2
(45) Date of Patent: Aug. 15, 2023

(54) PXR AGONISTS AND USES THEREOF FOR GUT BARRIER DYSFUNCTION TREATMENT AND PREVENTION

(71) Applicants: Albert Einstein College of Medicine, Bronx, NY (US); Drexel University, Philadelphia, PA (US); Palacky University Olomouc, Olomouc (CZ)

(72) Inventors: Sridhar Mani, Riverdale, NY (US); Felix Kopp, Brooklyn, NY (US); Zdenek Dvorak, Olomouc (CZ); Sandhya Kortagere, Newtown, PA (US); Chamini Karunaratne, Mamaroneck, NY (US)

(73) Assignees: Albert Einstein College of Medicine, Bronx, NY (US); Drexel University, Philadelphia, PA (US); Palacky University Olomouc, Olomouc (CZ)

( * ) Notice: Subject to any disclaimer, the term of this patent is extended or adjusted under 35 U.S.C. 154(b) by 0 days.

(21) Appl. No.: 16/478,653

(22) PCT Filed: Jan. 18, 2018

(86) PCT No.: PCT/US2018/014129
§ 371 (c)(1),
(2) Date: Jul. 17, 2019

(87) PCT Pub. No.: WO2018/136575
PCT Pub. Date: Jul. 26, 2018

(65) Prior Publication Data
US 2019/0367475 A1    Dec. 5, 2019

Related U.S. Application Data

(60) Provisional application No. 62/447,716, filed on Jan. 18, 2017.

(51) Int. Cl.
*A61P 1/00* (2006.01)
*C07D 401/06* (2006.01)
*C07D 209/12* (2006.01)
*C07D 471/04* (2006.01)

(52) U.S. Cl.
CPC .............. *C07D 401/06* (2013.01); *A61P 1/00* (2018.01); *C07D 209/12* (2013.01); *C07D 471/04* (2013.01)

(58) Field of Classification Search
CPC ........................................................ A61P 1/00
See application file for complete search history.

(56) References Cited

U.S. PATENT DOCUMENTS

2012/0232070 A1  9/2012  Amaudrut et al.
2015/0258151 A1  9/2015  Mani et al.

FOREIGN PATENT DOCUMENTS

WO    2011/030068 A1    3/2011
WO    2012/006477 A1    1/2012
WO    2014/088982 A1    6/2014

OTHER PUBLICATIONS

American Chemical Society. Chemical Abstract Service. RN 54851-93-3. First entered into STN (date of first public availability): Nov. 16, 1984. (Year: 1984).*
American Chemical Society. Chemical Abstract Service. RN #: 149227-00-9. Date of first public availability/first entered into STN: Aug. 11, 1993. (Year: 1993).*
American Chemical Society. Chemical Abstract Service. RN 79853-87-5. Date of first public availability/entered into STN on Nov. 16, 1984. (Year: 1984).*
American Chemical Society. Chemical Abstract Service. RN 1401915-29-4. Date of first public availability/entered into STN on Oct. 24, 2012. (Year: 2012).*
American Chemical Society. Chemical Abstract Service. RN 2075795-89-8. Date of first public availability/entered into STN on Feb. 24, 2017. (Year: 2017).*
American Chemical Society. Chemical Abstract Service. RN 1401976-89-3. Date entered into STN/first made available to public: Oct. 24, 2012. (Year: 2012).*
American Chemical Society. Chemical Abstract Service. RN 33037-90-0. First available to Public/Entered into STN on Nov. 16, 1984. (Year: 1984).*
American Chemical Society. Chemical Abstract Service. RN 66054-55-5. First available to Public/Entered into STN on Nov. 16, 1984. (Year: 1984).*
American Chemical Society. Chemical Abstract Service. RN 19984-20-4. First available to Public/Entered into STN on Nov. 16, 1984. (Year: 1984).*
Santra, S., Jat, B., and Santra, P.K. "Synthesis and Antimicrobial Activities of Chaicones and Indole Derived from Acetyl Pyridines." Asian Journal of Chemistry. (2018), vol. 30, No. 4, pp. 883-888. (Year: 2018).*
Teague, S "Implications of Protein Flexibility for Drug Discovery", Nature Reviews Drug Discovery, 2003, vol. 2, pp. 527-541.
Hubbard et al.. "Adaptation of the human aryl hydrocarbon receptor to sense microbiota-derived indoles", Scientific Reports. 2015; 5:12689, 13 pages.
Dhayalan et al., "One-Pot Synthesis of 1-Phenylsulfonyl-2-aroylindoles", Synthetic Communications, vol. 42, No. 3, 2011, pp. 402-411.
Cooper et al., "Nucleophilic Substitutions at an Indole beta-position", J.C.S. Chem. Comm., No. 13, 1977, pp. 432-434.
Sundberg et al., "A Novel Case of Stereoisomerism Dependent on Sterically Restrained Conformations", J Org Chem., vol. 40, No. 18, 1975, pp. 2613-2621.

* cited by examiner

*Primary Examiner* — John S Kenyon

(57) ABSTRACT

Small molecule agonists of the pregnane X receptor (PXR), compositions and methods are disclosed for treating or preventing gut barrier dysfunction, an illness associated with gut barrier dysfunction, toxic or inflammatory injury to intestines, or leaky intestinal (gut) syndrome in a subject.

13 Claims, 16 Drawing Sheets
Specification includes a Sequence Listing.

SEQUENCE LISTING

<160> NUMBER OF SEQ ID NOS: 1

<210> SEQ ID NO 1
<211> LENGTH: 434
<212> TYPE: PRT
<213> ORGANISM: Homo sapiens

<400> SEQUENCE: 1

```
Met Glu Val Arg Pro Lys Glu Ser Trp Asn His Ala Asp Phe Val His
1               5                   10                  15

Cys Glu Asp Thr Glu Ser Val Pro Gly Lys Pro Ser Val Asn Ala Asp
            20                  25                  30

Glu Glu Val Gly Gly Pro Gln Ile Cys Arg Val Cys Gly Asp Lys Ala
        35                  40                  45
```

```
Thr Gly Tyr His Phe Asn Val Met Thr Cys Glu Gly Cys Lys Gly Phe
    50                  55                  60

Phe Arg Arg Ala Met Lys Arg Asn Ala Arg Leu Arg Cys Pro Phe Arg
65                  70                  75                  80

Lys Gly Ala Cys Glu Ile Thr Arg Lys Thr Arg Arg Gln Cys Gln Ala
                85                  90                  95

Cys Arg Leu Arg Lys Cys Leu Glu Ser Gly Met Lys Lys Glu Met Ile
            100                 105                 110

Met Ser Asp Glu Ala Val Glu Glu Arg Arg Ala Leu Ile Lys Arg Lys
            115                 120                 125

Lys Ser Glu Arg Thr Gly Thr Gln Pro Leu Gly Val Gln Gly Leu Thr
            130                 135                 140

Glu Glu Gln Arg Met Met Ile Arg Glu Leu Met Asp Ala Gln Met Lys
145                 150                 155                 160

Thr Phe Asp Thr Thr Phe Ser His Phe Lys Asn Phe Arg Leu Pro Gly
                165                 170                 175

Val Leu Ser Ser Gly Cys Glu Leu Pro Glu Ser Leu Gln Ala Pro Ser
            180                 185                 190

Arg Glu Glu Ala Ala Lys Trp Ser Gln Val Arg Lys Asp Leu Cys Ser
            195                 200                 205

Leu Lys Val Ser Leu Gln Leu Arg Gly Glu Asp Gly Ser Val Trp Asn
            210                 215                 220

Tyr Lys Pro Pro Ala Asp Ser Gly Gly Lys Glu Ile Phe Ser Leu Leu
225                 230                 235                 240

Pro His Met Ala Asp Met Ser Thr Tyr Met Phe Lys Gly Ile Ile Ser
                245                 250                 255

Phe Ala Lys Val Ile Ser Tyr Phe Arg Asp Leu Pro Ile Glu Asp Gln
            260                 265                 270

Ile Ser Leu Leu Lys Gly Ala Ala Phe Glu Leu Cys Gln Leu Arg Phe
            275                 280                 285

Asn Thr Val Phe Asn Ala Glu Thr Gly Thr Trp Glu Cys Gly Arg Leu
            290                 295                 300

Ser Tyr Cys Leu Glu Asp Thr Ala Gly Gly Phe Gln Gln Leu Leu Leu
305                 310                 315                 320

Glu Pro Met Leu Lys Phe His Tyr Met Leu Lys Lys Leu Gln Leu His
                325                 330                 335

Glu Glu Glu Tyr Val Leu Met Gln Ala Ile Ser Leu Phe Ser Pro Asp
            340                 345                 350

Arg Pro Gly Val Leu Gln His Arg Val Val Asp Gln Leu Gln Glu Gln
            355                 360                 365

Phe Ala Ile Thr Leu Lys Ser Tyr Ile Glu Cys Asn Arg Pro Gln Pro
            370                 375                 380

Ala His Arg Phe Leu Phe Leu Lys Ile Met Ala Met Leu Thr Glu Leu
385                 390                 395                 400

Arg Ser Ile Asn Ala Gln His Thr Gln Arg Leu Leu Arg Ile Gln Asp
                405                 410                 415

Ile His Pro Phe Ala Thr Pro Leu Met Gln Glu Leu Phe Gly Ile Thr
            420                 425                 430

Gly Ser
```

PXR AGONISTS AND USES THEREOF FOR GUT BARRIER DYSFUNCTION TREATMENT AND PREVENTION

CROSS REFERENCE TO RELATED APPLICATIONS

This application claims the benefit of U.S. Provisional Patent Application No. 62/447,716, filed on Jan. 18, 2017, the contents of which are hereby incorporated by reference.

FIELD OF THE INVENTION

The invention relates to non-toxic, small molecule agonist compounds and their use for activation of the pregnane X receptor (PXR) for preventing or alleviating toxic or inflammatory injury to the intestines, and treating the "leaky" intestinal (gut) syndrome.

BACKGROUND OF THE INVENTION

Throughout this application various publications are referred to in parentheses. Full citations for these references may be found at the end of the specification before the claims. The disclosures of these publications are hereby incorporated by reference in their entireties into the subject application to more fully describe the art to which the subject application pertains.

Gut barrier dysfunction is linked to a broad spectrum of human ailments (1-5). Increased permeability of the gut wall can result, for example, from toxins, poor diet, parasites, infection, or medications (5). Leaky gut syndrome is a term for enhanced intestinal permeability, which can occur in patients susceptible to a multitude of diseases ranging, for example, from inflammatory bowel disease to autoimmune systemic ailments. Patients who develop dysbiosis or bacterial overgrowth, or who are on long-term antibiotics or are generally susceptible to inflammatory diseases of the gut are likely to have enhanced intestinal permeability as a pathogenic cause driving future associations with disease onset. Orphan nuclear receptors can serve as a link between the host environment and gut immunity. One such receptor is the pregnane X receptor (PXR) (NR1I2; also termed SXR, PAR). PXR is the primary xenobiotic sensor in human and mammalian tissues. It responds to a wide range of structurally- and chemically-distinct ligands (6-16).

The intestinal lumen is lined by intestinal epithelial cells (IEC), which serve as an effective barrier between the lumen and the deep underlying tissue called the lamina propria (LP). In addition to providing host defense against invading pathogens and toxins, IECs play a pivotal role in maintaining immune homeostasis. Several investigators have demonstrated that cross talk between heterodimeric nuclear receptors regulates inflammation (17-21). Data from rodent studies show that PXR is an established modifier (therapeutic target) of inflammation and healing in irritable bowel disease (IBD) (22-25). This conclusion stems from the observations that PXR ligands, regardless of chemical class, protect wild-type mice but not PXR knockout mice against DSS- (or TNBS-) mediated colitis and colitis-mediated colon cancer (25-37). The intestines of PXR$^{-/-}$ mice show sub-clinical inflammation that is severely aggravated by stress (33). Accordingly, there is a clear propensity towards a reduction in PXR mRNA expression in inflamed tissues, particularly in childhood Crohn's disease and adulthood ulcerative colitis (33, 38-40). Furthermore, reports have shown an association of PXR haplotypes and SNPs to IBD in humans. However, this remains to be validated by meta-analyses and functional studies (41-45). PXR when unliganded (in its Apo-form) is excluded from nuclear entry and is inactive in both mouse cells and tissues; however, when it is ligand tethered, PXR trans locates to the nucleus where it acts as a RXR heterodimeric transcription factor complex. In humans, PXR can be nuclear even in its Apo-form (46).

Several PXR ligands exist and could be developed as potential therapeutics (e.g., rifaximin as a PXR ligand for IBD) (47-50, 73); however, they are plagued by chemical toxicity (e.g., drug-induced cytotoxicity like paclitaxel) (16) or the potential for off-target toxicity (e.g., activation of nuclear receptors like LXR that accentuate the toxicity of PXR in the liver e.g., T0901317) (51, 52). As a result, prolonged use of these drugs in the clinic (e.g., rifaximin and hepatic steatosis, drug resistance) is not efficacious (48, 53). Certain parental pharmacologic features of newer ligands (e.g., antibiotic class, flame retardant class) make these compounds less suitable for clinical development unless safety is clearly evident (54-57). The indoles and metabolites are PXR ligands, but there is significant room to improve their potency, pharmacokinetic properties and receptor activation profiles. Thus, a new pharmacologic class of drugs with a high potential to be safe is warranted.

The present invention addresses the need for non-toxic, small molecule compounds for treating and preventing gut barrier dysfunction and illnesses associated with gut barrier dysfunction, such as inflammatory bowel disease, irritable bowel syndrome, fatty liver disease, non-alcoholic fatty liver disease, colon cancer, cardiovascular, pulmonary and autoimmune disease.

SUMMARY OF THE INVENTION

The invention provides non-toxic, small molecule agonists of the pregnane X receptor (PXR), compositions and methods for treating or preventing gut barrier dysfunction, an illness associated with gut barrier dysfunction, toxic or inflammatory injury to intestines, or leaky intestinal (gut) syndrome in a subject.

DETAILED DESCRIPTION OF THE INVENTION

Figure 1A:
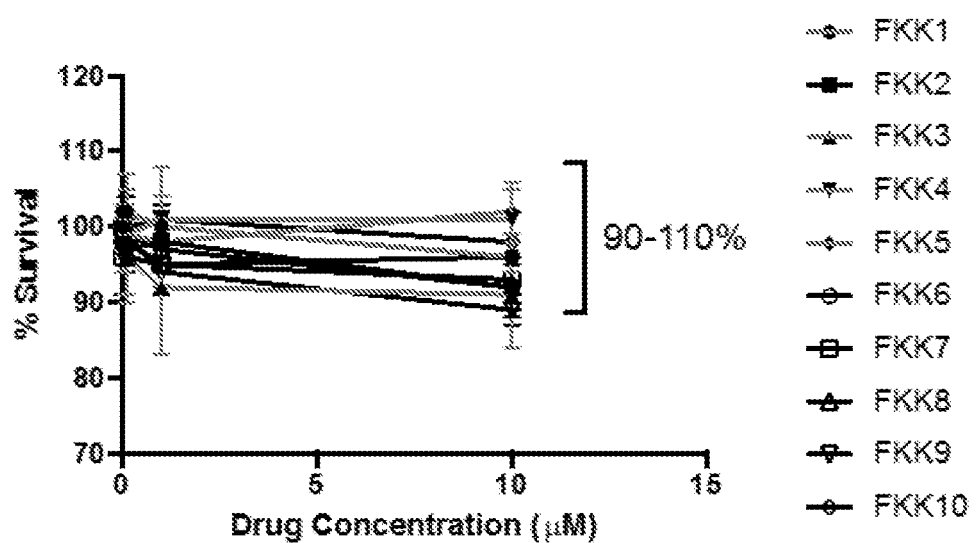
FIG. 1A-1B. FKK compound cytotoxicity assay. (A) MTT cell cytotoxicity assay in LS180 cells lines (NCBI Bookshelf: world wide web ncbi.nlm.nih.gov/books/NBK144065/). The cell survival for all the compounds is between 90-110% over a 24 h incubation period. (B) LDH release assay performed in plated hepatocytes after a 24 h and 48 h exposure. For both panels, assays were performed at least two times in triplicate.

The invention provides a compound having the structure of formula (I)

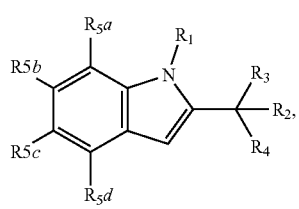

(I)

wherein
$R_1$ is H, $SO_2Ph$, alkoxy, ethoxymethyl or

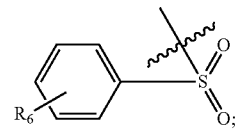

$R_2$ is H, 2-indolyl, 1-prop-1-ynyl, 3-prop-1-ynyl or 4-pyridyl;
$R_3$ is OH; O-alkyl or =O;
$R_4$ is

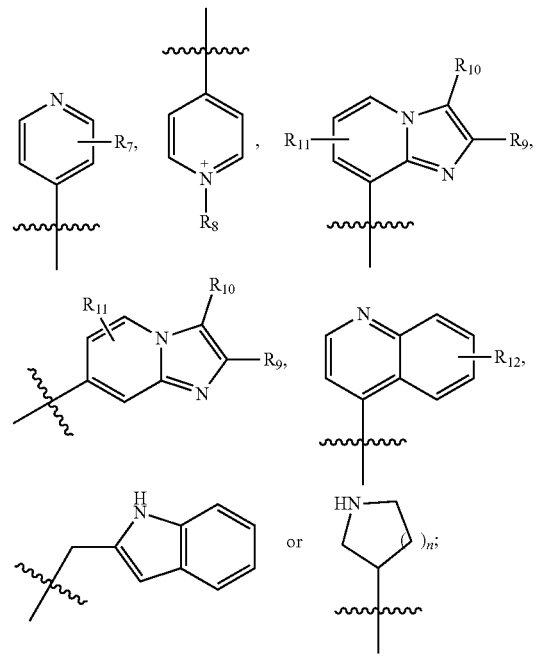

$R_{5a}$, $R_{5b}$, $R_{5c}$ and $R_{5d}$ are each independently halogen, alkyl, alkoxy, $NH_2$, NHR, $NHR_2$, OH, phenyl, or phenyl substituted with one or more alkyl, halogen, OH or $NH_2$;
$R_6$ is H, halogen, alkyl, alkoxy, $NH_2$, NHR, $NHR_2$, $CF_3$ or OH;
$R_7$ is H, halogen, alkyl, alkoxy, $NH_2$, NHR, $NHR_2$ or $CF_3$;
$R_8$ is alkyl;
$R_9$, $R_{10}$ and $R_{11}$ are each independently H, halogen, alkyl, alkoxy, $NH_2$, NHR, $NHR_2$, OH, phenyl, or phenyl substituted with one or more alkyl, halogen, OH or $NH_2$;
$R_{12}$ is H, halogen, alkyl, alkoxy, $NH_2$, NHR, $NHR_2$, OH, phenyl, or phenyl substituted with one or more alkyl, halogen, OH or $NH_2$;
R is alkyl;
n is 1 or 2; and ~~~ represents the point of attachment to the scaffold;
or a pharmaceutically acceptable salt thereof.

"Ph" is an abbreviation for "phenyl." Each halogen is independently Br, Cl, F or I. Each alkyl is preferably and independently C1-C6 alkyl or C1-C3 alkyl.

The compound can have, for example the structure selected from the group consisting of formulas (II)-(XVIII):

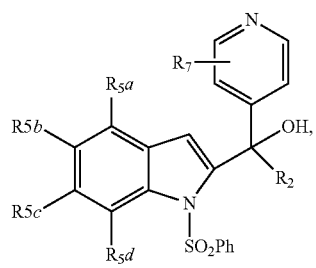
(II)
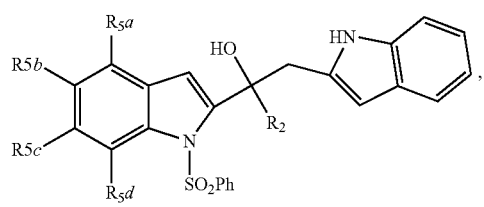
(III)
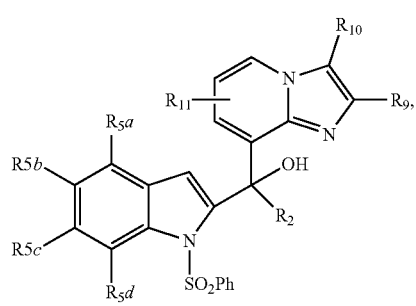
(IV)
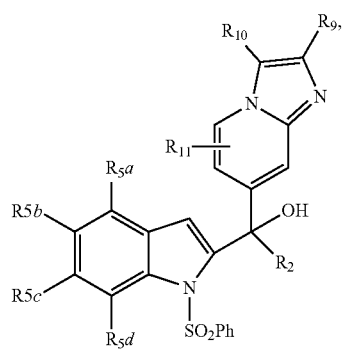
(V)
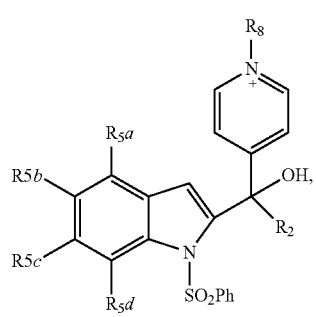
(VI)
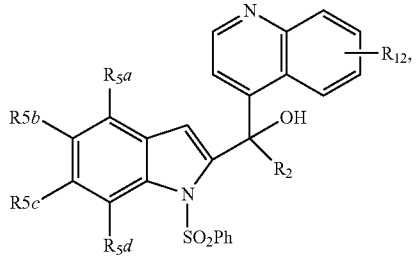
(VII)
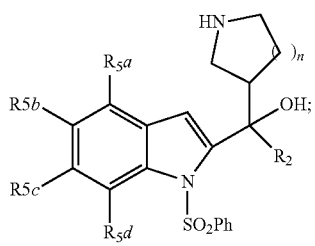
(VIII)
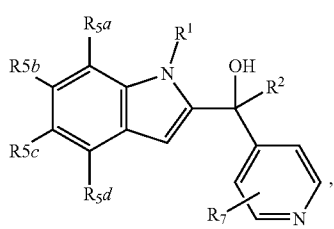
(IX)
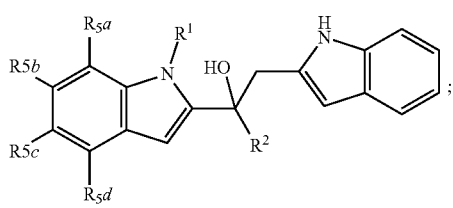
(X)
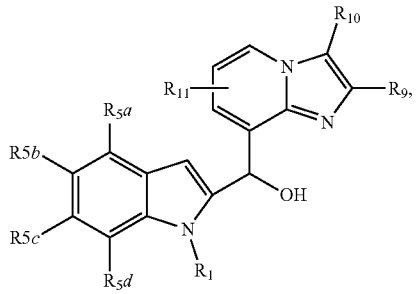
(XI)
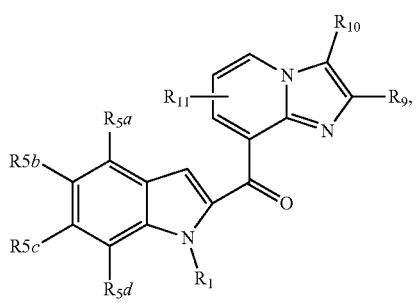
(XII)

-continued
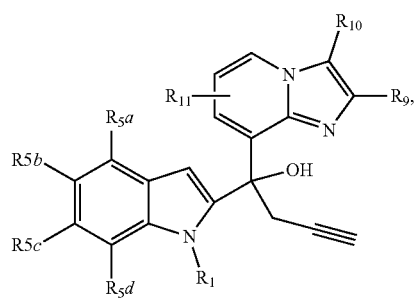
(XIII)
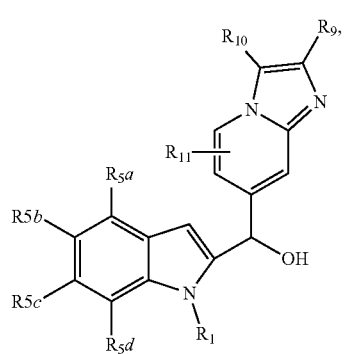
(XIV)
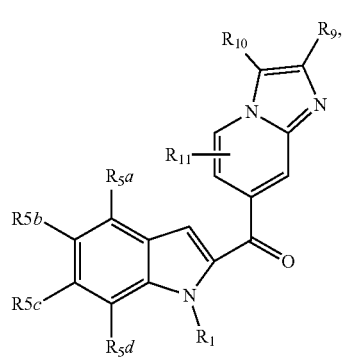
(XV)
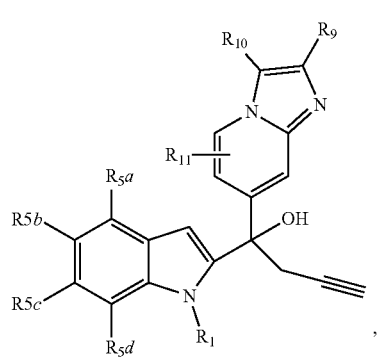
(XVI)
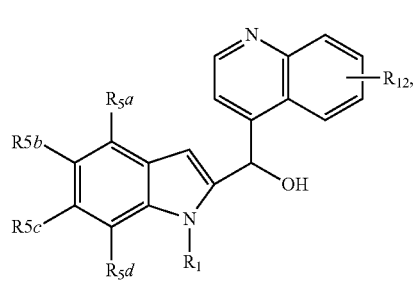
(XVII)
-continued
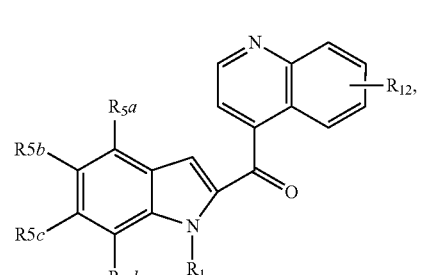
(XVIII)
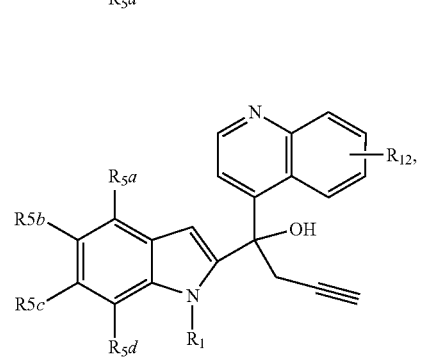
(XIX)
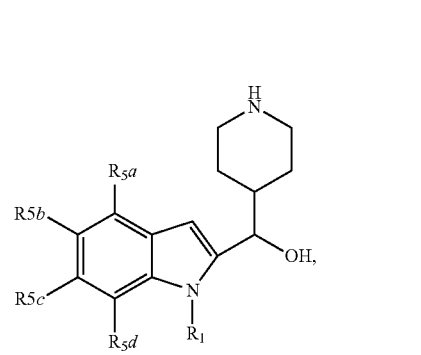
(XX)
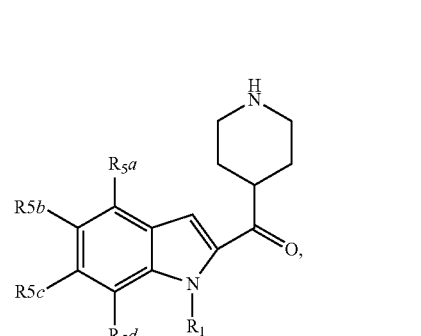
(XXI)
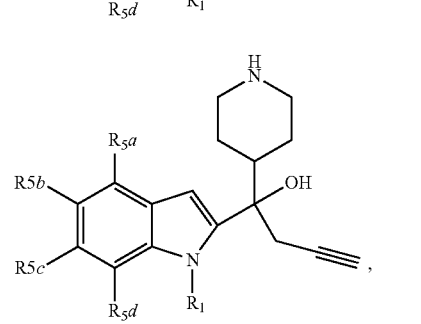
(XXII)

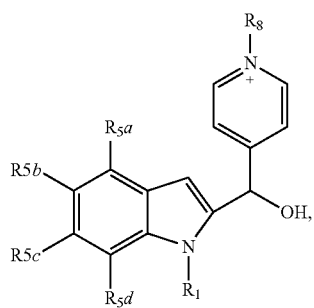
(XXIII)
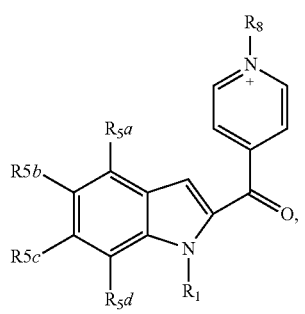
(XXIV)
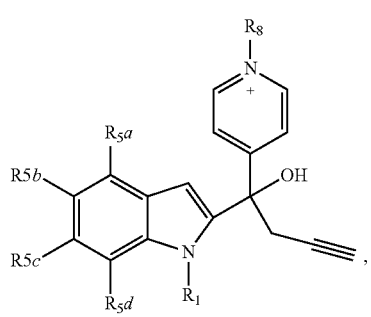
(XXV)
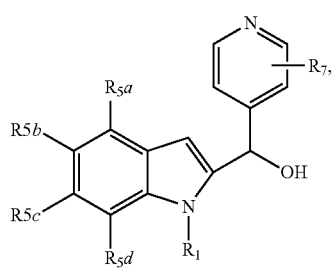
(XXVI)
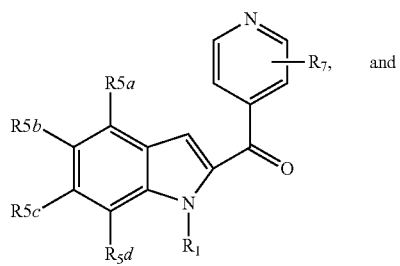
(XXVII) and
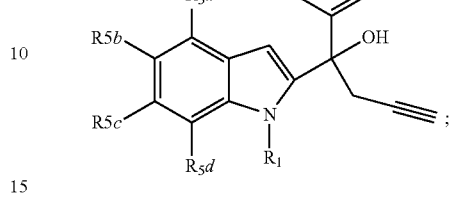
(XXVIII)
or a pharmaceutically acceptable salt thereof.
The compound can have the structure selected from the group consisting of
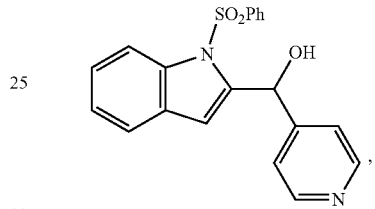
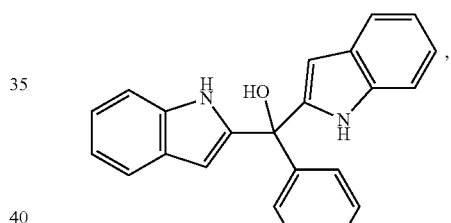
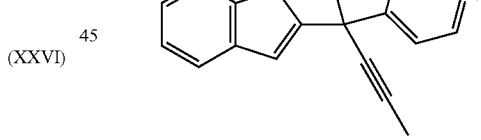
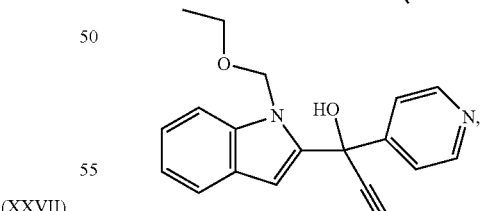
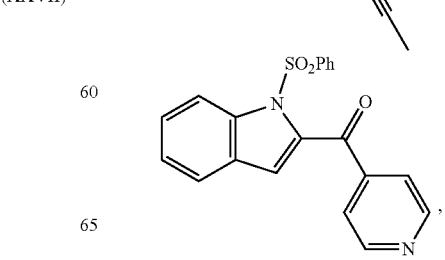

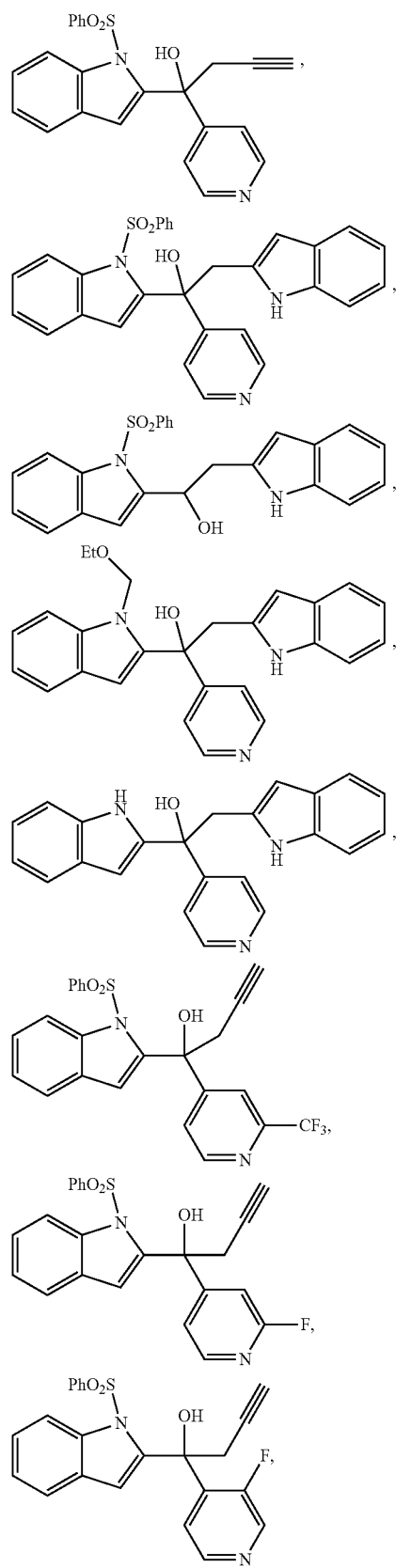
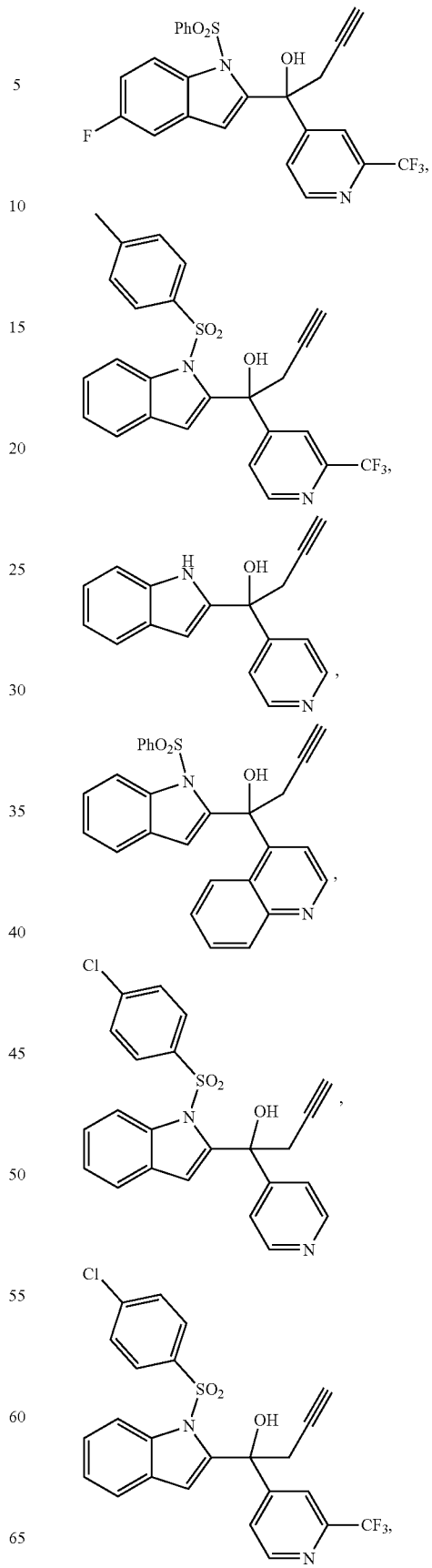

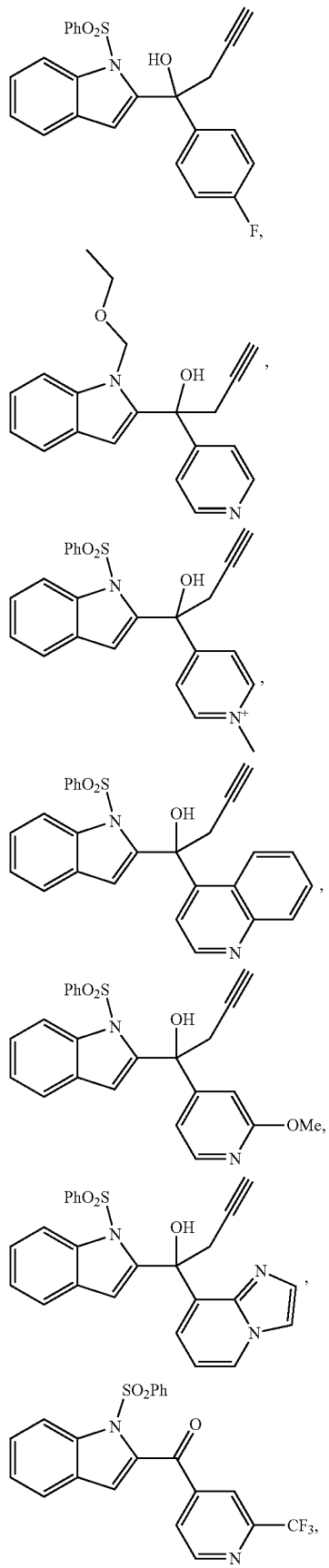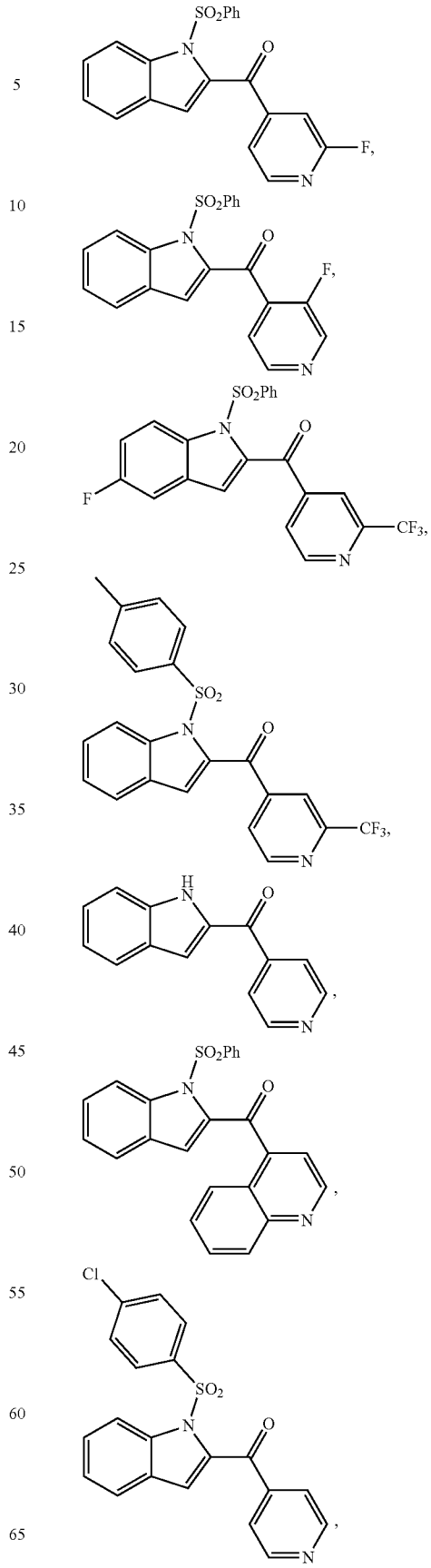

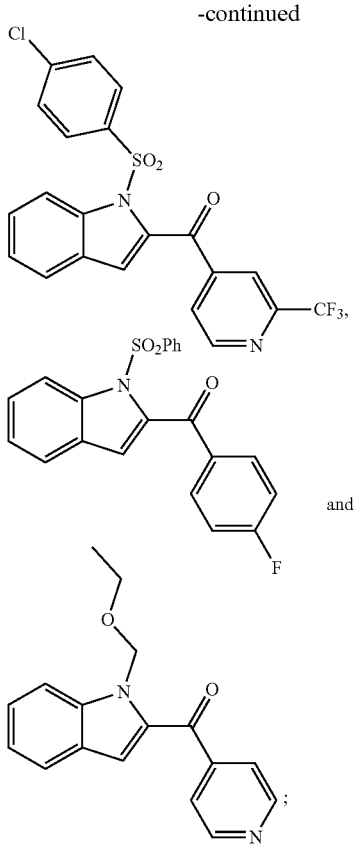

or a pharmaceutically acceptable salt thereof.

Preferably, the compound binds to and activates pregnane X receptor (PXR).

Pharmaceutically acceptable salts that can be used with compounds of the present invention include non-toxic salts derived, for example, from inorganic or organic acids including, but not limited to, salts derived from hydrochloric, sulfuric, phosphoric, acetic, lactic, fumaric, succinic, tartaric, gluconic, citric, methanesulphonic and p-toluenesulphonic acids.

The invention also provides a pharmaceutical composition comprising one or more of the compounds disclosed herein and a pharmaceutically acceptable carrier or diluent. The pharmaceutical composition can, for example, comprise the following compounds

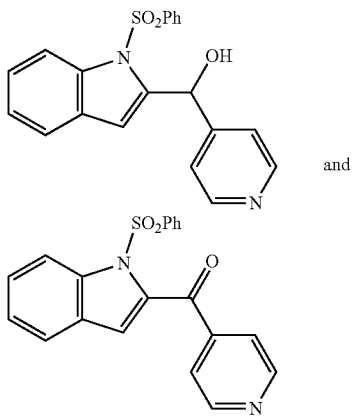

or pharmaceutically acceptable salts thereof.

Pharmaceutically acceptable carriers and diluents that can be used herewith encompasses any of the standard pharmaceutical carriers or diluents, such as, for example, a sterile isotonic saline, phosphate buffered saline solution, water, and emulsions, such as an oil/water or water/oil emulsions.

The pharmaceutical compositions can be formulated to be advantageous for the selected route of administration to a subject. Preferred compositions are formulated for oral or rectal administration.

The invention provides a method of treating or preventing gut barrier dysfunction, an illness associated with gut barrier dysfunction, toxic or inflammatory injury to intestines, or leaky intestinal (gut) syndrome in a subject comprising administering to the subject one or more of the compounds disclosed herein in an amount effective to treat or prevent gut barrier dysfunction, an illness associated with gut barrier dysfunction, toxic or inflammatory injury to intestines, or leaky intestinal (gut) syndrome in a subject.

As used herein, "treating" or "treat" a condition means to alleviate or ameliorate or eliminate a sign or symptom of the condition that is being treated. "Preventing" or "prevent" a condition means that in a subject who is free of the condition, reducing the risk of the subject developing the condition or reducing the severity of the condition that the subject develops compared to the severity of the condition that would develop in the absence of administering the compound to the subject.

The subject can have, for example, irritable bowel syndrome, inflammatory bowel disease, intestinal allergic syndrome or celiac sprue. The subject can be at risk for developing gut barrier dysfunction, or an illness associated with gut barrier dysfunction, due to, for example, exposure to a toxin, a medication, poor diet, an infection such as a parasite infection or a bacterial infection, dysbiosis, bacterial overgrowth, or long-term use of an antibiotic.

An illnesses associated with gut barrier dysfunction can be, for example, inflammatory bowel disease, irritable bowel syndrome, fatty liver disease, colon cancer, cardiovascular disease, pulmonary disease and/or autoimmune disease.

The method can comprise administering the following compounds to the subject

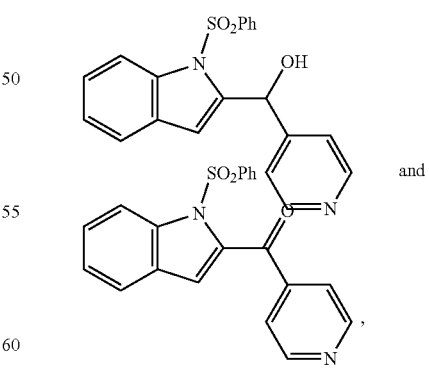

or pharmaceutically acceptable salts thereof.

The subject can be any animal and is preferably a human.

Human PXR has the amino acid sequence (SEQ ID NO:1, Accession: O75469.1 GI: 6093860)

```
  1 mevrpkeswn hadfvhcedt esvpgkpsvn adeevggpqi crvcgdkatg yhfnvmtceg 61 ckgffrramk rnarlrcpfr kgaceitrkt rrqcqacrlr kclesgmkke mimsdeavee 121 rralikrkks ertgtqplgv qglteeqrmm irelmdaqmk tfdttfshfk nfrlpgvlss 181 gcelpeslqa psreeaakws qvrkdlcslk vslqlrgedg svwnykppad sggkeifsll 241 phmadmstym fkgiisfakv isyfrdlpie dqisllkgaa felcqlrfnt vfnaetgtwe 301 cgrlsycled taggfqqlll epmlkfhyml kklqlheeey vlmqaislfs pdrpgvlqhr 361 vvdqlqeqfa itlksyiecn rpqpahrflf lkimamltel rsinaqhtqr llriqdihpf 421 atplmqelfg itgs.
```

The compounds and compositions of the present invention can be administered to subjects using routes of administration known in the art. The administration can be systemic or localized to a specific site. Routes of administration include, but are not limited to, intravenous, intramuscular, intrathecal or subcutaneous injection, oral or rectal administration, and injection into a specific site. Preferred routes of administration include oral or rectal administration.

All combinations of the various elements described herein are within the scope of the invention unless otherwise indicated herein or otherwise clearly contradicted by context.

Where a numerical range is provided herein, it is understood that all numerical subsets of that range, and all the individual integers contained therein, are provided as part of the invention.

This invention will be better understood from the Experimental Details that follow. However, one skilled in the art will readily appreciate that the specific methods and results discussed are merely illustrative of the invention as described more fully in the claims that follow thereafter.

Experimental Details

Designing Novel PXR Activators Using Indole-IPA Combined Pharmacophore

Indole and indole-3-propionic acid (IPA) were co-docked to the hPXR crystal structure and a four point combined pharmacophore was designed using the interaction profile of indole and IPA. The 4-point pharmacophore was then used to screen a library of vendor available small molecules, and 5 hit molecules that strictly obeyed the pharmacophore were docked into the ligand binding domain (LBD) of PXR using GOLD (version 4.3), and the complexes were scored using goldscore and chemscore functions. In order to test the predictions, two commercially available molecules FKK999 and BAS451 (Ryan Scientific), which had docking scores of 65.89 and 52.66, respectively, were chosen for testing. The structures of these compounds are indicated below:

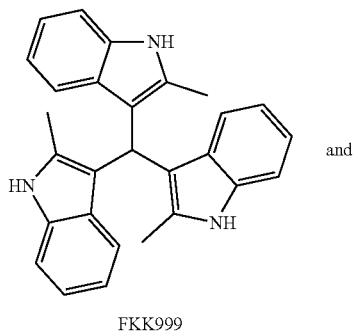

FKK999 and

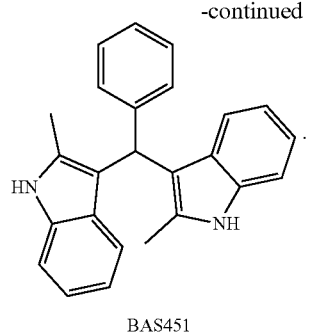

BAS451

Docking studies orient them in the binding pocket of PXR to maximize their interactions with the residues from LBD. The main interactions include a ring stacking interaction with Trp299 and main chain hydrogen bonded interactions with Cys284 and Met246. In addition, the three indole rings have favorable hydrophobic interactions with several residues such as Leu304, Phe288, Tyr306, Met243, Met250 and electrostatic interactions with Glu300, Ser305, Glu321, Gln285 and Ser247, which most likely contribute to the high binding score of FKK999. Docking of BAS451 shows several shared interactions with those of FKK999, but does not include key ring stacking interaction with Trp299 and electrostatic interactions that contribute to the binding efficacy since BAS451 has only two indole rings and the additional phenyl ring does not compensate for the lost interactions.

Two molecules that were readily available (Ryan Scientific: FKK999 & BAS451) were purchased and tested in vitro for PXR activation using a HepG2 reporter assay. The results suggested that FKK999 robustly activated PXR ($EC_{50}$ 5+0.5 μM); however, compound BAS451 had no effect ($EC_{50}$ not reached at 50M) in the same assay. Rifampicin has been used for these assays since this compound is a strong positive control and known agonist for human PXR (58, 59). Using the LS180 cell line, these results were independently confirmed (60-71). In general, reporter cell lines are efficient ways to screen for PXR ligands (72). In the LS180 intestinal cell line, the PXR activation assay involves a transient transfection system using a specific PXR plasmid and reporter plasmid ($CV_{max}$ % 11.2+2; $CV_{mid}$ % 10.8+0.1.4; Signal Window 6.2+1.1; Z' factor 0.51+0.005).

Based on the interaction profile of FKK999, a 10-membered compound library was designed and synthesized based on three distinct scaffolds (Table 1).

TABLE 1

Library of compounds.

1a: $R_1$ = H; $R_2$ = 2-indolyl  FK-2
1b: $R_1$ = $SO_2Ph$; $R_2$ = H  FK-1
1c: $R_1$ = $SO_2Ph$; $R_2$ = 3-prop-1ynyl  FK-6
1d: $R_1$ = $SO_2Ph$; $R_2$ = 1-prop-1ynyl  FK-3
1e: $R_1$ = EOM; $R_2$ = 1-prop-1ynyl  FK-4
EOM = ethoxymethyl.

2a: $R_1$ = $SO_2Ph$; $R_2$ = 4-py  FK-7
2b: $R_1$ = EOM; $R_2$ = 4-py  FK-9
2c: $R_1$ = H; $R_2$ = 4-py  FK-10
2d: $R_1$ = $SO_2Ph$; $R_2$ = H  FK-8

3 FK-5

Synthetic Routes

Scheme 1 summarizes the final routes that were used to access first generation compounds. In the first step, lithium reagent was generated by treating EOM-protected indole with n-butyllithium, and reacted with picolyl ester, to obtain tertiary alcohol. To remove the EOM protection, the compound was then treated with trifluoroacetic acid (TFA) in $CH_2Cl_2$. These conditions surprisingly just cleaved the terminal ethyl ethers of the EOM groups. The remaining hemiaminals, however, proved unstable to basic conditions and were easily removed with LiOH in MeOH, to yield one compound. The synthesis of the second compound started out from the same protected indole which was lithiated and reacted with 4-pyridine carbaldehyde. Subsequent Dess-Martin oxidation afforded a ketone. Freshly prepared propargylmagnesium bromide was added at 0° C. to obtain propargyl alcohol. A Sonogashira coupling with 2-iodoaniline, followed by the established EOM deprotection protocol then set the stage for the formation of the second indole moiety.

Various conditions were screened (e.g.: KH, NMP; Cu, THF; $PdCl_2$, $CH_3CN$; AgOTf, $CH_3CN$) for this pivotal cyclization and the treatment with silver triflate in acetonitrile at elevated temperatures gave the best results. Using microwave heating helped to speed up the reaction and to improve the isolated yields. It is worth noting, that this cyclization works for both the protected and unprotected precursors. However, attempts to deprotect the cyclized intermediate remained unsuccessful, which made it necessary to deprotect prior to cyclization. The first generation compounds as well as a small fragment collection were evaluated for their activities.

Scheme 1

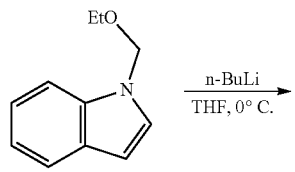

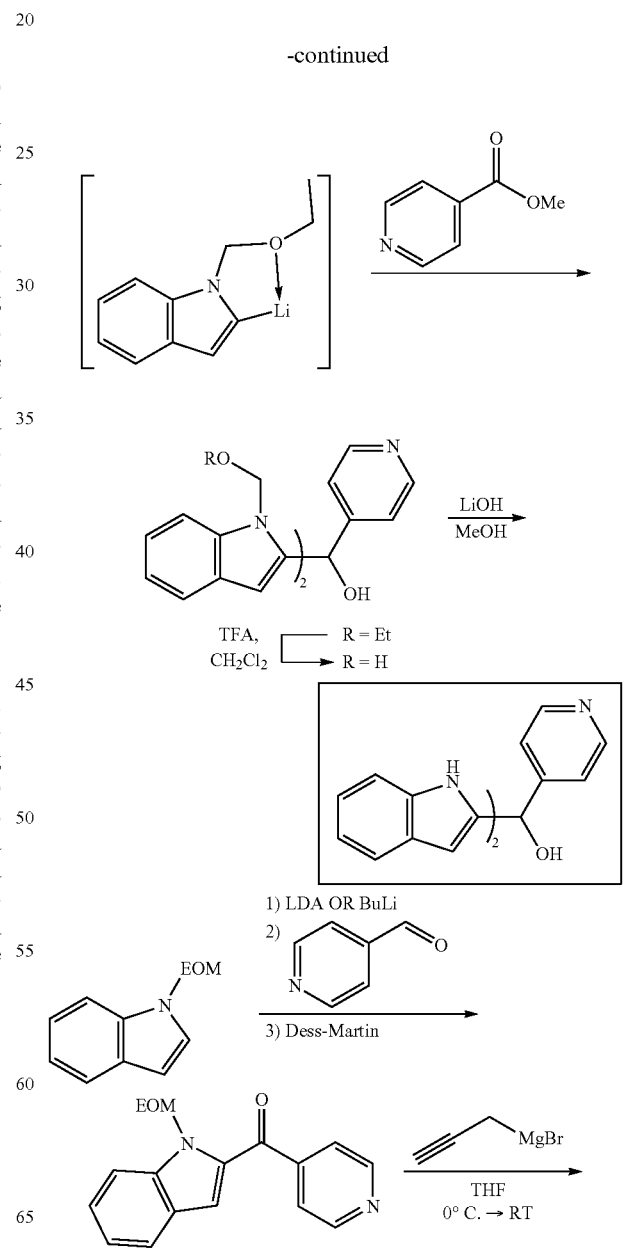

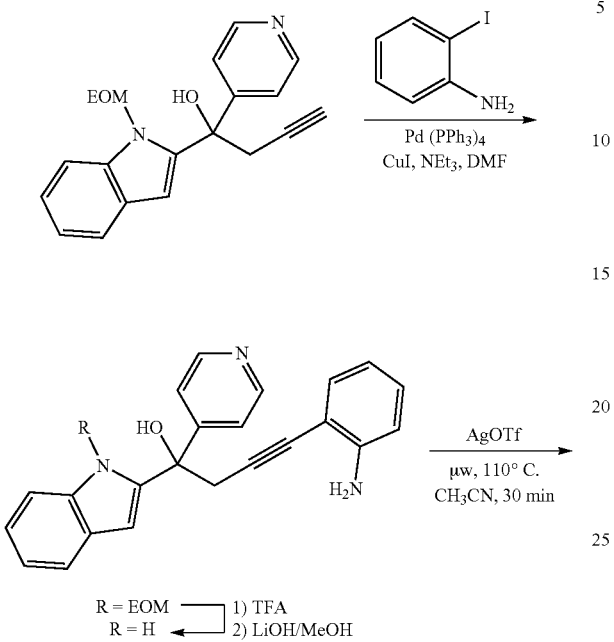

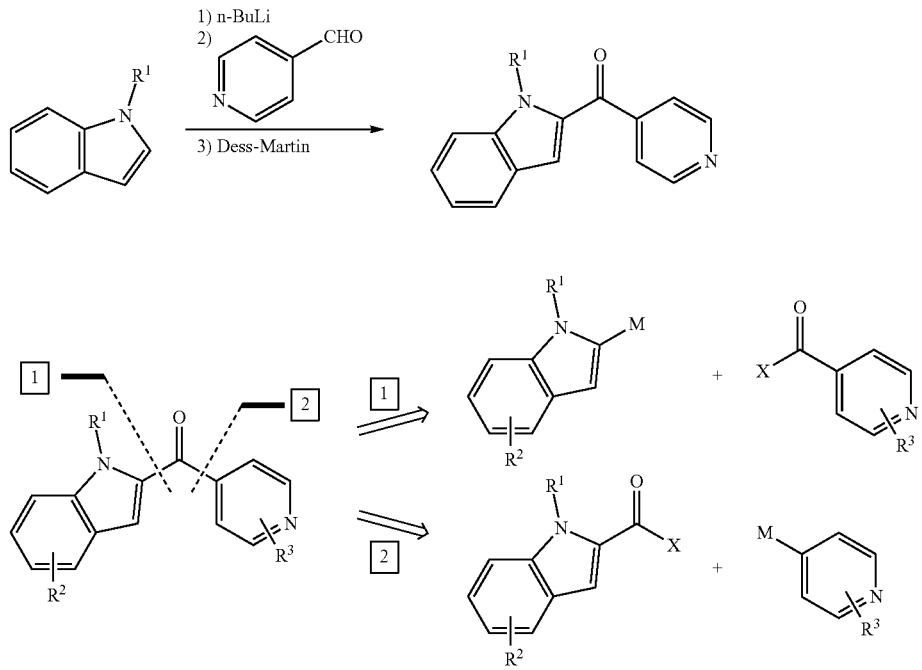

The compound shown in Scheme 2 can be assembled by reacting 2-lithiated indoles with isonicotinaldehyde, followed by Dess-Martin oxidation of the resulting carbinol (Scheme 2, left). However, there are two useful retrosynthetic disconnections to be considered (Scheme 2, right). Other than a 2-metalated indole (disconnection 1), a 4-metalated pyridine (disconnection 2) can also be used and reacted with the corresponding electrophile. The most common electrophiles to be considered in both retrosynthetic variants are acid chlorides (eventually with CuI catalysis) and aldehydes. In the latter case, subsequent oxidation of the resulting carbinols is required. Complexing protecting groups, like EOM or $SO_2Ph$ were needed in the original route to direct the lithiation into the 2-position of the indole. Furthermore, the use of lithium-organic reagents limited the range of functional groups that can be tolerated. The use of magnesium- and zinc-organic reagents (74-77) allows for more diverse choices for $R^1$, as well as the introduction of more complex and sensitive functional groups.

The addition of magnesium-organic reagents to proceeds smoothly and with good yields. As shown in Scheme 3, prop-2-yn-1-ylmagnesium bromide was added to furnish a carbinol. 2-3 more synthetic steps were required to access the illustrated scaffolds. To rapidly explore the structural space occupied by these scaffolds further, one can use the intermediate terminal alkyne in a series of Cu-catalyzed Azide-Alkyne Cycloaddition (CuAAC) reactions. In the resulting analogs, the triazole ring will structurally resemble the five membered ring of the indole moiety, while R³ represents the variable part.

Scheme 3. Introduction of additional diversity using Grignarrd reagents and CuAAC reactions.

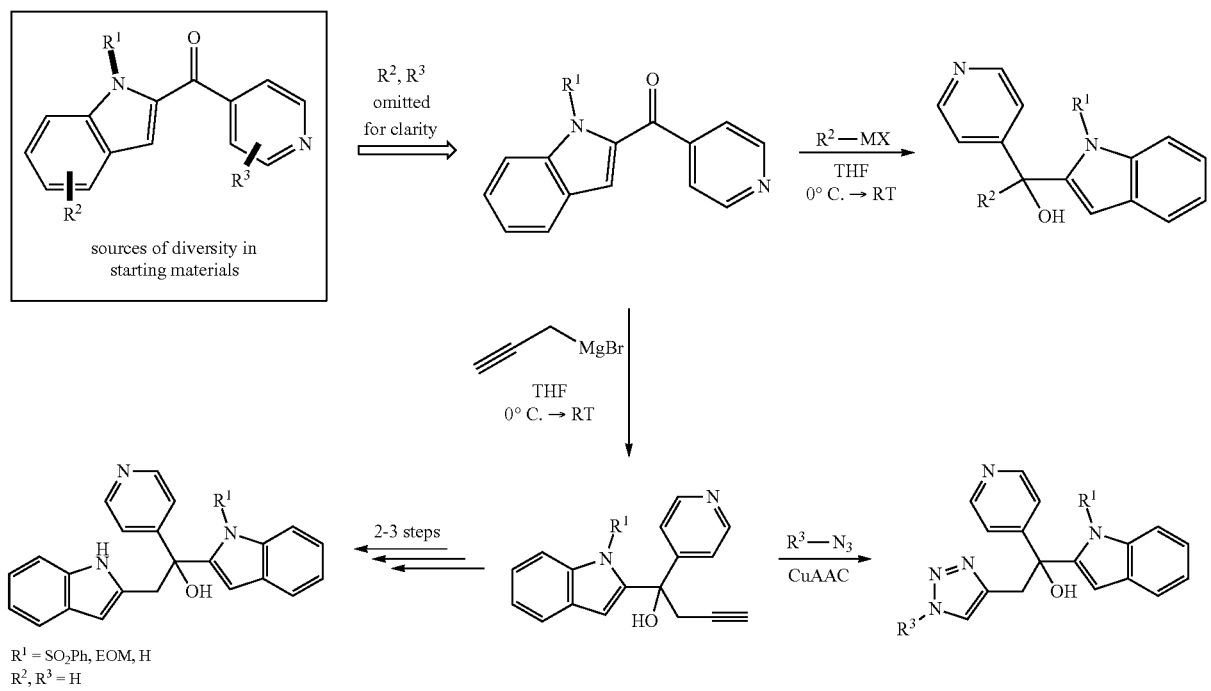

Biological Activity of Compounds

Compounds were tested for their effect on PXR transactivation in two different in vitro systems. Their structures are indicated below, along with the structure of FK999. The prefixes FKK and FK- are used interchangeably to refer to these compounds.

FK-1

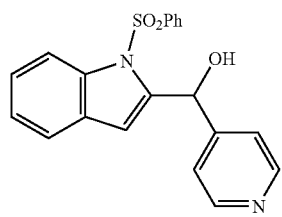

FK-2

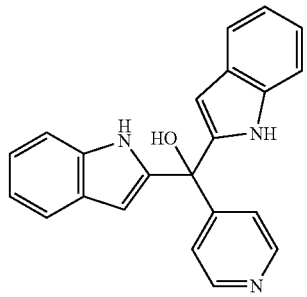

FK-3

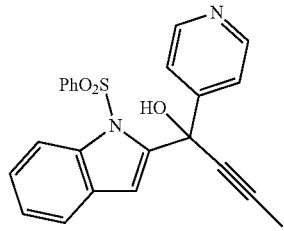

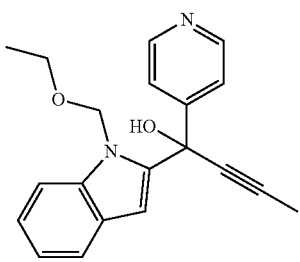

FK-4

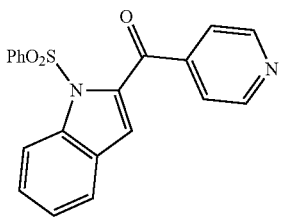

FK-5

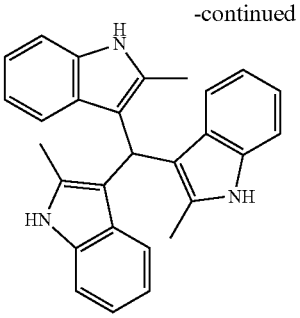

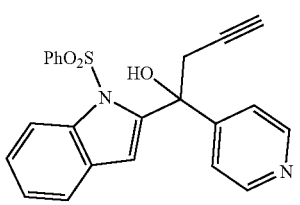

FK-6

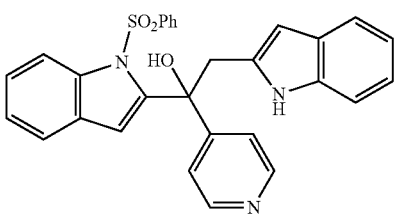

FK-7

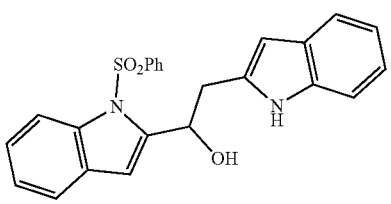

FK-8

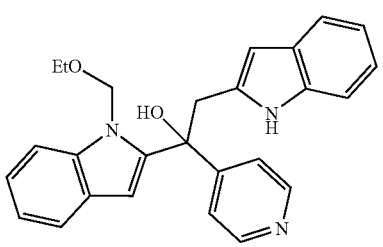

FK-9

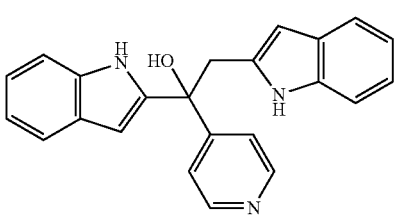

FK-10

Figure 1B:
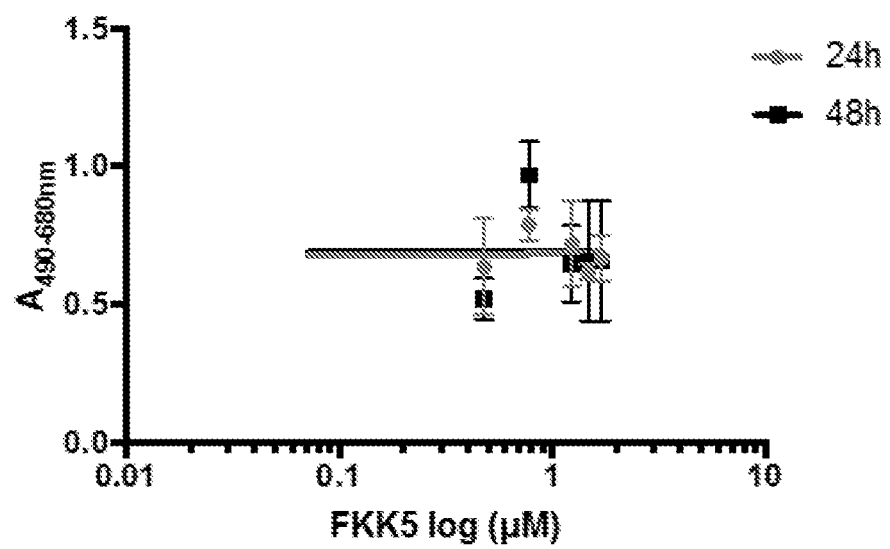
Figures 2A, 2B, 2C, 2D, 2E, 2F:
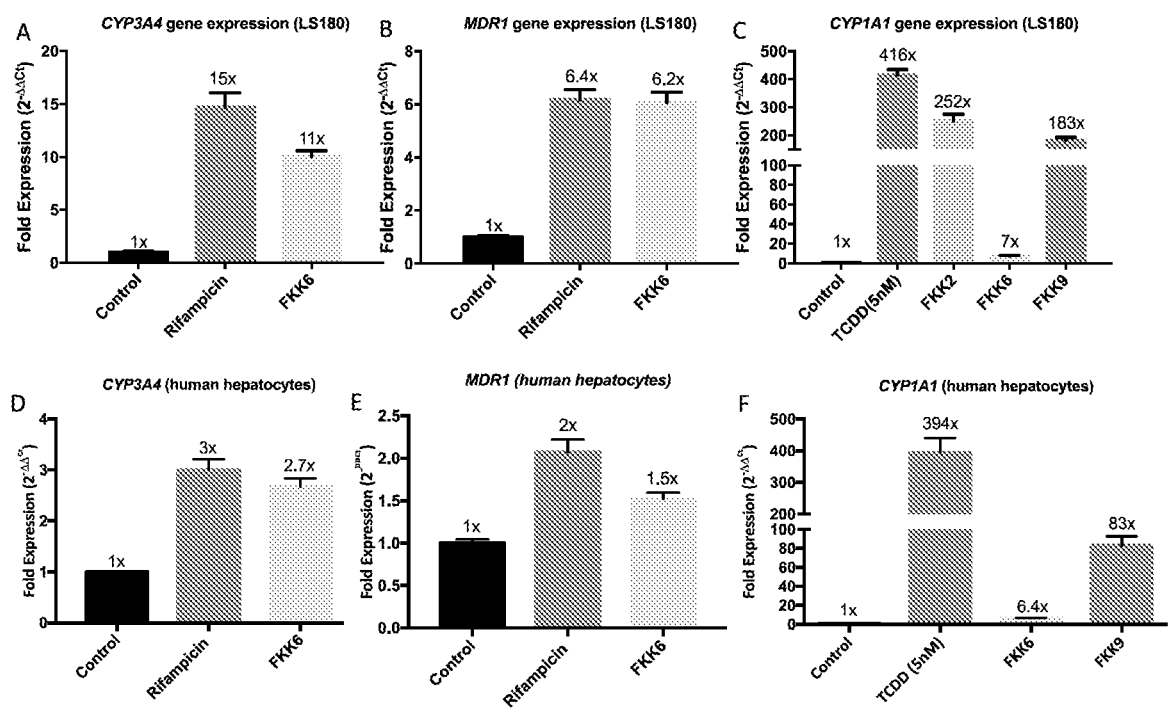
FIG. 2A-2F. FKK6 induced PXR and AhR target gene expression in (A-C) LS180 cell lines and (D-F) human hepatocytes in culture. PXR target genes (CYP3A4, MDR1) and AhR target gene (CYP1A1) mRNA expression after 24 h incubation with 10 µM FKK6 in PXR-transfected LS180 cells and human hepatocytes as indicated. The mRNA expression was determined using RT-qPCR (SYBR green) and primers well established from prior papers. The ΔΔCt method was used to calculate fold expression of mRNA. Histogram, mean±SD. Representative triplicate experiment is shown from at least three independent reproducible experiments.

The FKK series of compounds is extremely well tolerated by LS 180 intestinal cells in culture, and there is no cytotoxicity observed when hepatocytes are incubated with FKK5 (FIG. 1). As a further example, FKK6 ($EC_{50}$ 0.88 µM and $E_{max}/E_{max[rifampicin,\ positive\ control]}$ 117% in LS180 cells; PXR transactivation data not shown) induces PXR target genes: CYP3A4 (~10 fold), MDR1 (>6 fold), and negligible AhR target gene CYP1A1 in PXR-transfected LS180 cells. In plated human hepatocytes, FKK6 (hydroxyl modification of FKK5) induces PXR target genes: CYP3A4 (~2.6 fold), MDR1 (~1.5 fold), and negligible activation of the AhR target gene CYP1A1 (FIG. 2). A very unique feature of simple indole structures (FKK1-10) is that they are predicted to have very short systemic residence times limiting systemic drug exposure and any potential for off-target effects in organs other than the intestines (78).

Figure 3:
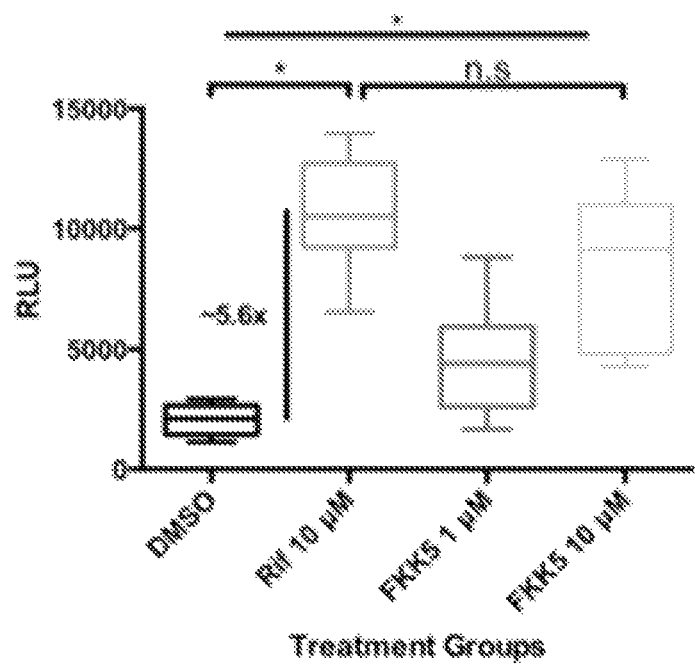
FIG. 3. One-hybrid PXR reporter gene assay. Performed in Caco-2 cells as a 24 h exposure to FKK5 at two different concentrations.

FKK5, activated PXR but not AhR in a HTS nuclear receptor activation screen using LS180 cells (data not shown; $EC_{50}$ 1.68 µM and $E_{max}/E_{max[rifampicin,\ positive\ control]}$ 128%); which was validated using a one-hybrid PXR LBD reporter assay (FIG. 3; ~5 fold activation of PXR). Indeed, combinatorial studies show that with small indoles combining FKK1 (1 µM) with FKK5 (1 µM) yields synergistic activation of PXR (~4 fold).

Figure 4:
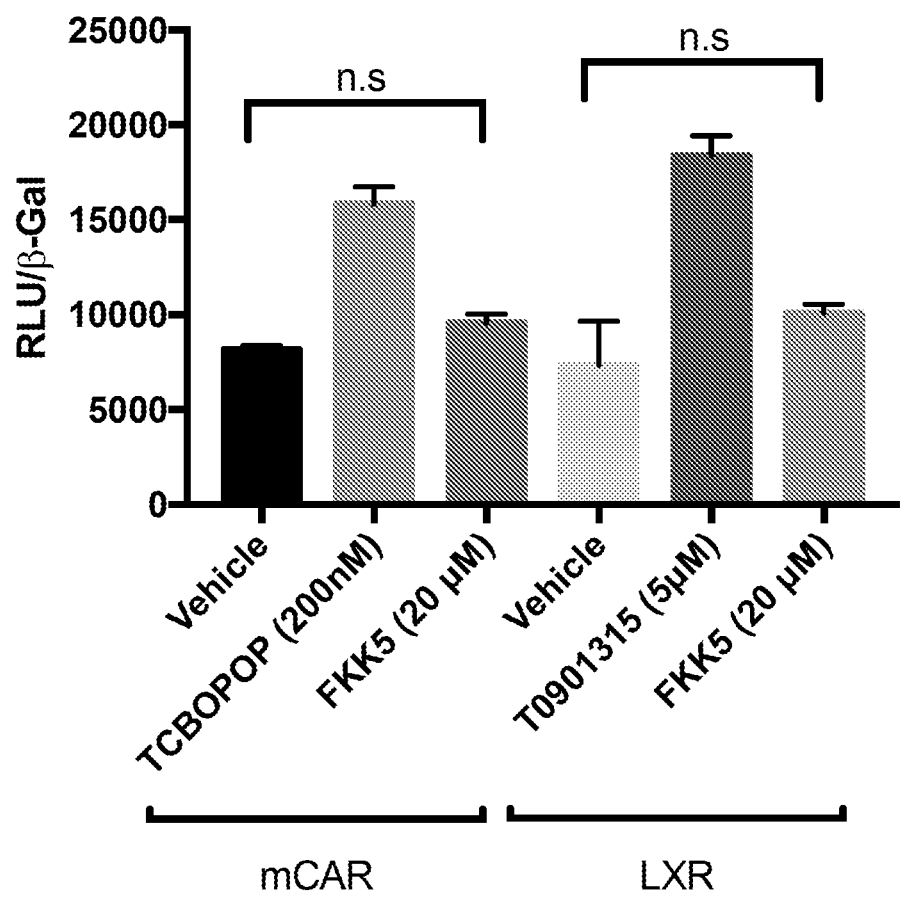
FIG. 4. Nuclear Receptor transactivation assays in caco-2 (day 0) cells. Methods used are published (33). Assays were performed at least two times in triplicate CAR, constitutive androstane receptor; TCBOPOP, CAR ligand; LXR, Liver X receptor; T0901315, LXR ligand. n.s, not significant.
Figure 5:
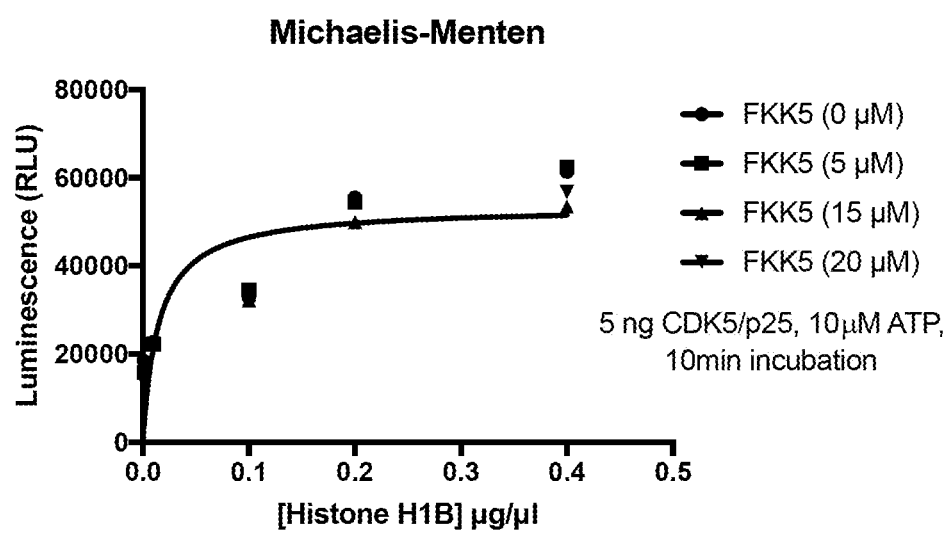
FIG. 5. ADP-Glo kinase with CDK5/p25 enzyme. Michaelis-Menton fit of RLU values across FKK5 concentrations after enzyme and time of incubation was optimized. The fit is nearly similar with one curve describing all concentration effects. Km~0.01483; Ki~4.656e+099; Vmax~53380.

IPA/Indoles can have weak (~2 fold) but important effects on the activation of other nuclear receptors (e.g., CAR, LXR) (33). Interestingly, IPA does not activate AhR and this is in agreement with a prior publication (81) and in the context of indole (which activates AhR), metabolites can actually suppress AhR function (82). Some receptors, specifically CAR and LXR, can act to induce liver steatosis (79, 83-86) and hepatocarcinogenesis (CAR) (80, 84, 87-89) and thus, avoiding excessive activation of these nuclear receptors in the context of PXR activation would be important. Interestingly, FKK5 does not activate LXR or CAR; in fact, with increasing concentrations of FKK5, CAR function is inhibited (FIG. 4). FKK5 (up to 20 µM) also does not inhibit CDK5/p25 enzyme (FIG. 5). CDK5 (along with CDK2) are important kinases that phosphorylate and inhibit PXR activation (90). Accordingly, based on the data, it is unlikely that FKK5 activates PXR via inhibition of CDK5.

Characterization of FKK Compounds as hPXR and/or AhR Agonists.

Figure 6A:
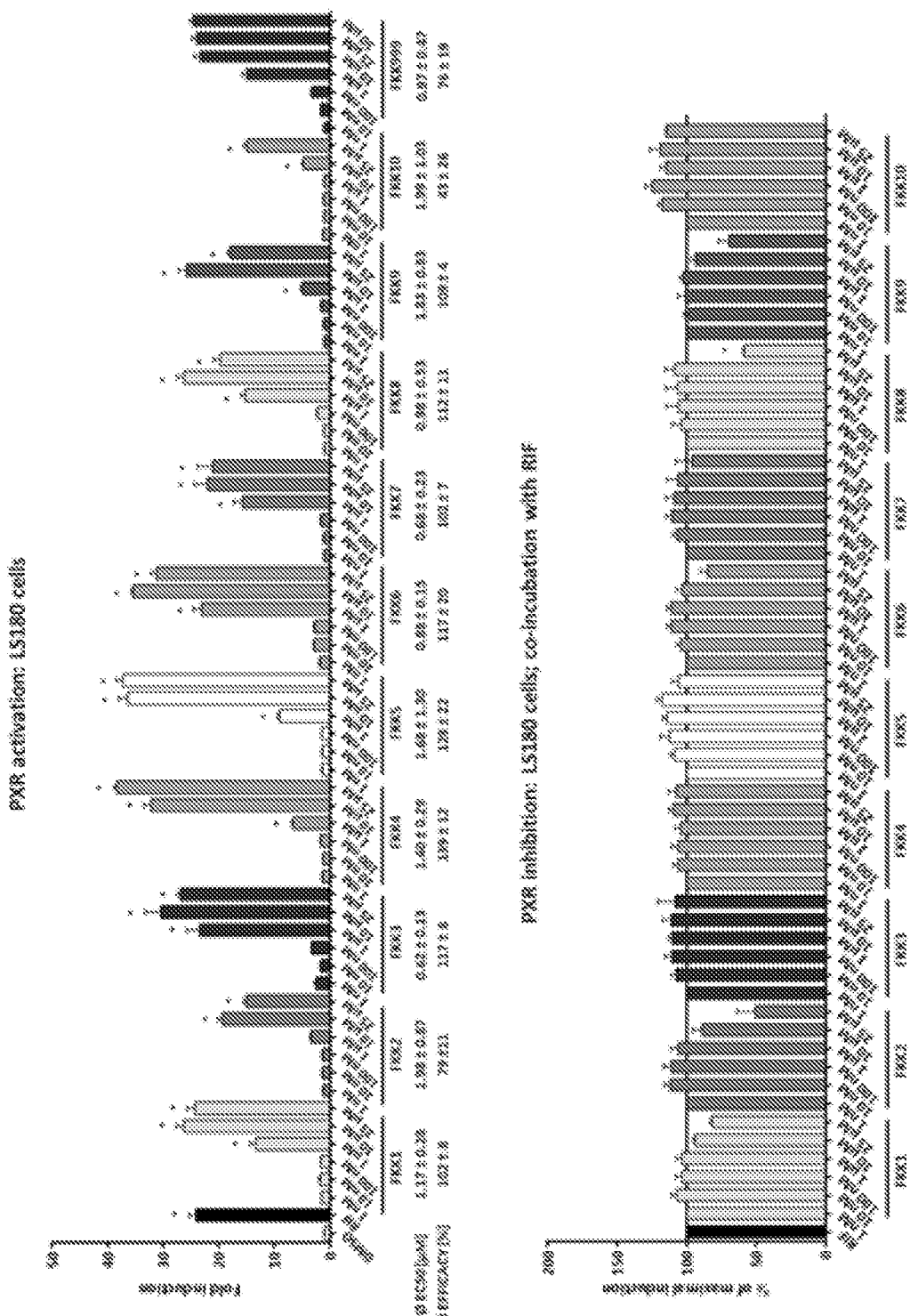
FIG. 6A-6E. Activation and inhibition studies with different FKK compounds. (A) PXR activation, LS180 cells (upper), and PXR inhibition, LS180 cells, co-incubation with RIF (lower). (B) AhR activation, AZ-AHR cells (upper), and AhR inhibition, AZ-AHR cells, co-incubation with TCDD (lower). (C) GR activation, AZ-GR cells (upper), and VDR activation, IZ-VDRE cells (lower). (D) TR activation, PZ-GR cells (upper), and AR activation, AIZ-AR cells (lower). (E) Displacement of radiolabeled 9-cis-retinoic acid (RA) by FKK compounds.
Figure 6B:
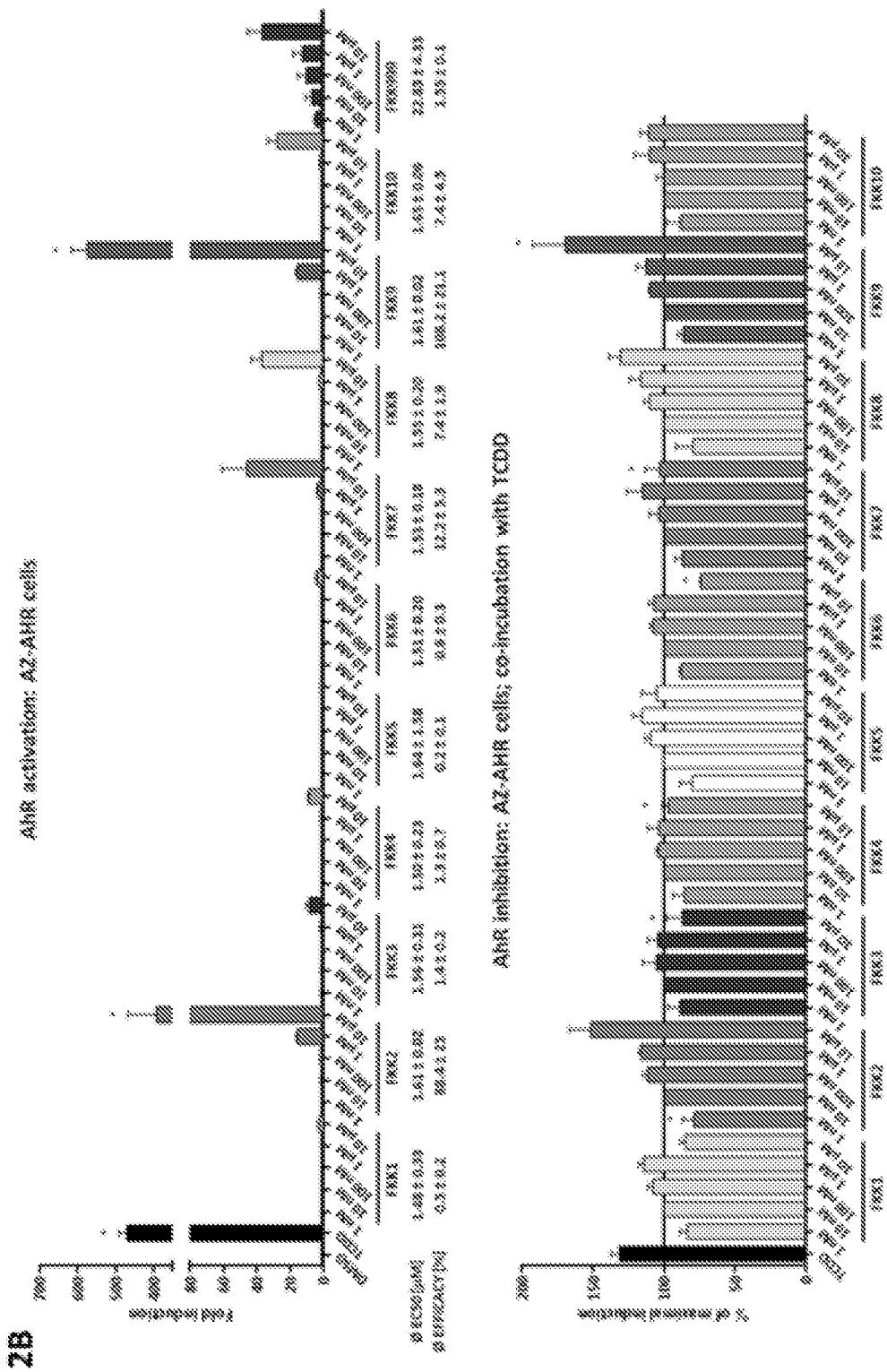
Figure 6C:
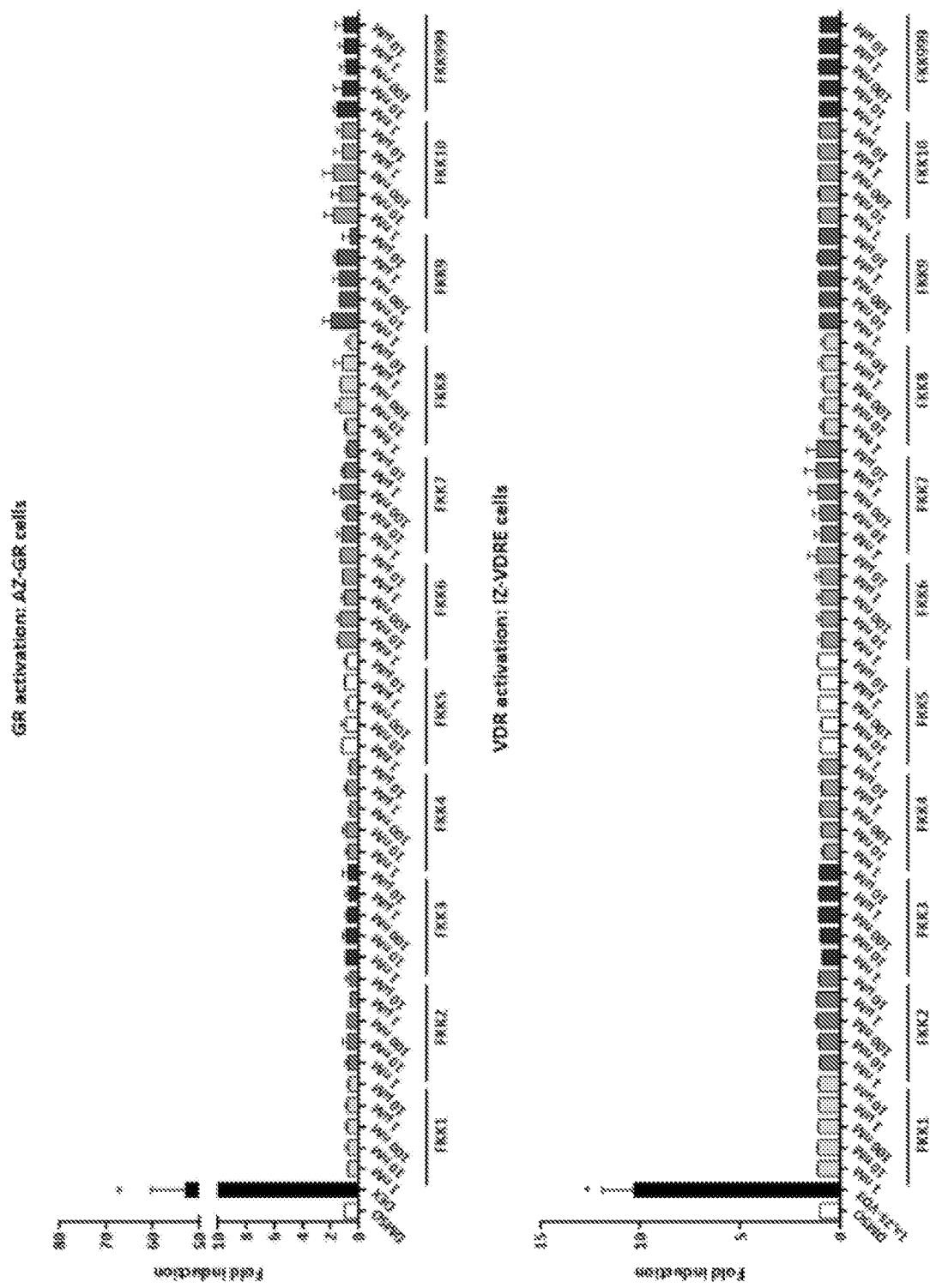
Figure 6D:
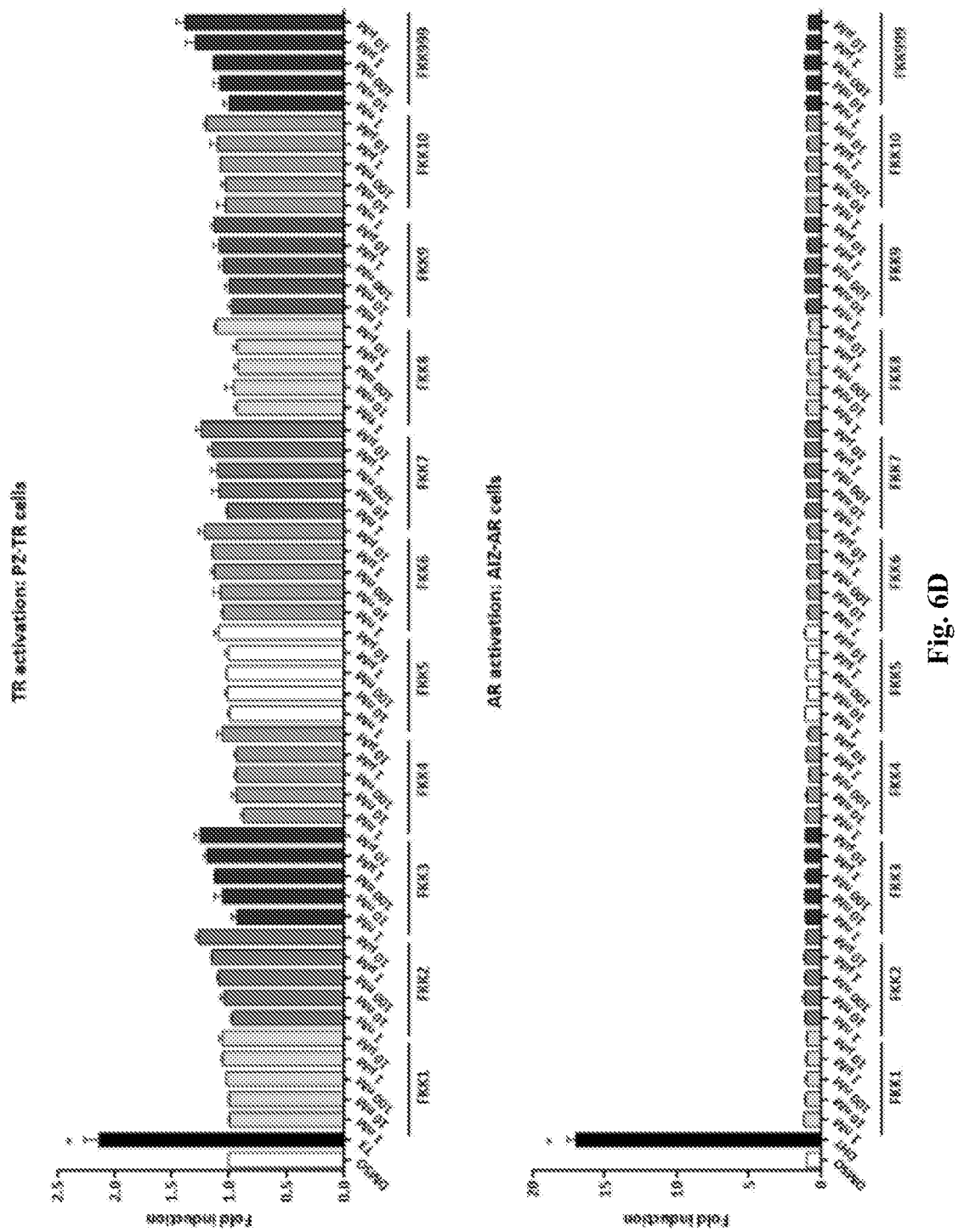
Figure 6E:
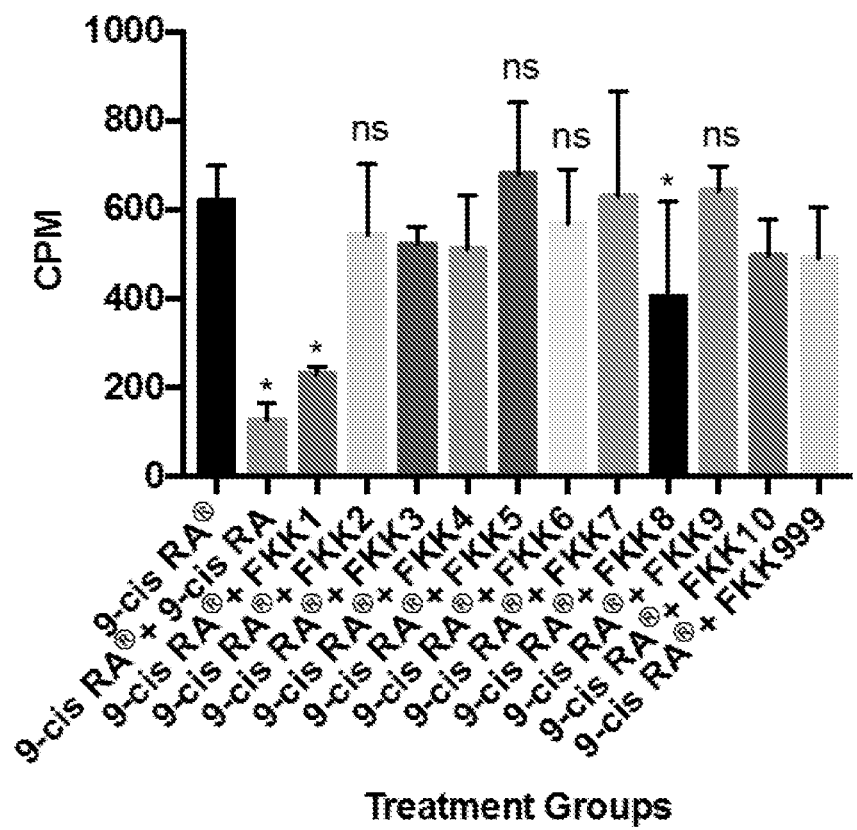

All the synthesized compounds and intermediates were tested for their potential to activate PXR and/or AhR via luciferase assays. The PXR activation assays were performed by co-transfecting full-length expressing human PXR plasmid (91) and p3A4 luciferase reporter (92) in LS180 or Caco-2 cells. AhR activation conducted using stably co-transfected HepG2 reporter cells as previously described (93). The results of these assays are shown in FIG. 6: all FKK compounds demonstrate a concentration-dependent effect on PXR activation, while only compound FKK 8 exhibited rifampicin-dependent PXR antagonism (inhibition) (FIG. 6A). By contrast, only FKK 2 and 9 at 10 µM, respectively, demonstrated significant (>100 fold) AhR activation comparable with dioxin (TCDD) control ligand. To a much lesser extent, variable degrees of dose-dependent AhR activation profiles were observed for FKK compounds 3, 4, 7, 8, 10 and 999 (FIG. 6B). With the exception of FKK6, there was no significant inhibition of TCDD-induced AhR activation. Compound FKK6 at 10 µM resulted in ~25% inhibition of maximal induction by TCDD. Independent verification of AhR activity of randomly selected compounds—FKK 5, 6 and 9—was performed in a separate laboratory (GHP). Nuclear receptor selectivity was assessed for FKK compounds for GR, ADR, TR and AR using cell-based luciferase assays previously described (93-102). There was no observed biologically significant (>2-fold) induction of nuclear receptor activity (FIG. 6C). RXR ligand displacement is only significant for FKK1 and FKK8 (FIG. 6D).

Gene Expression Assay Profile.

Figures 7A, 7B:
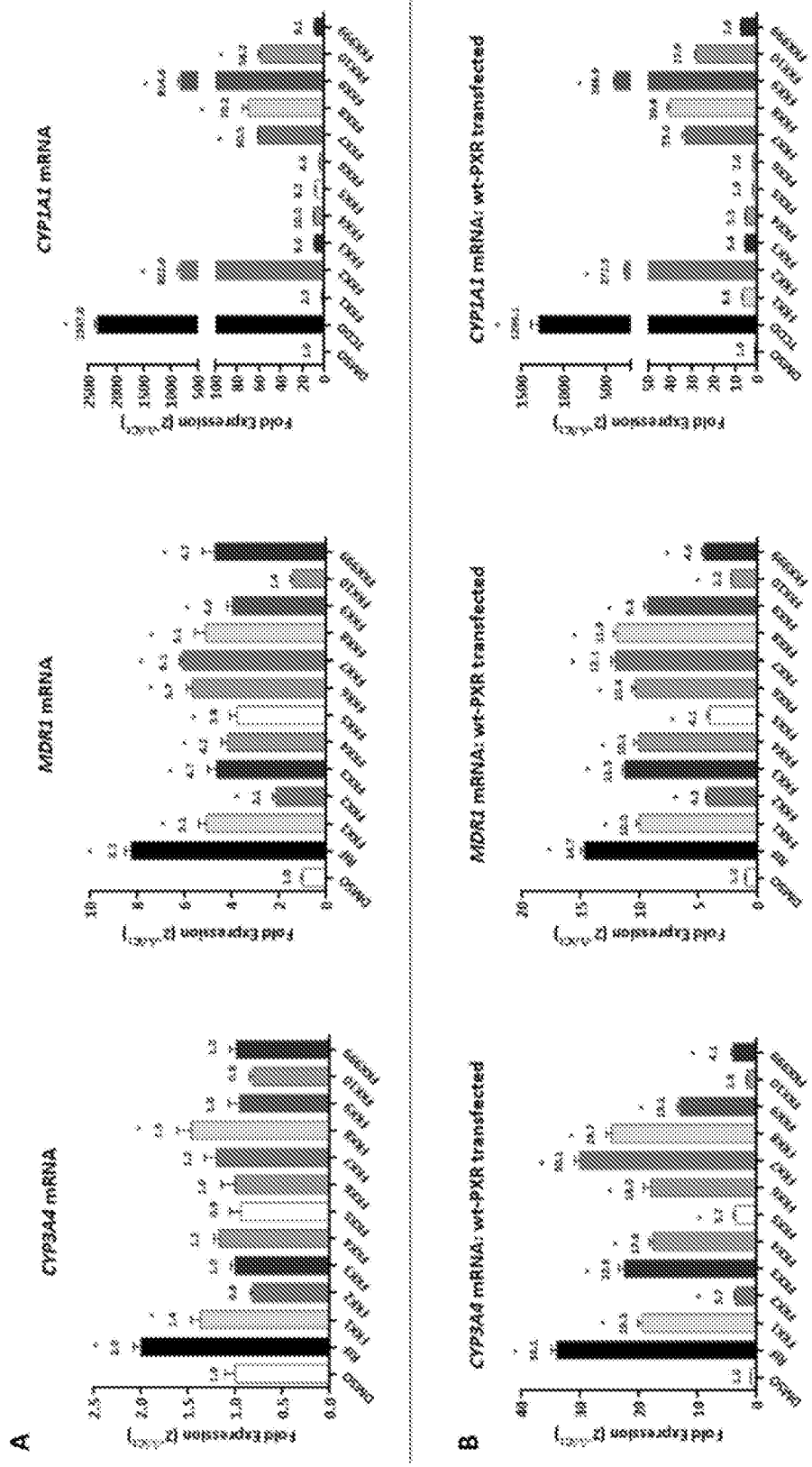
FIG. 7A-7B. Effects of FKK compounds on CYP3A4, MDR1 and CYP1A1 gene expression in LS180 cells. (A) mRNA expression. (B) mRNA expression in wt-PXR transfected cells.
Figures 8A, 8B, 8C, 8D:
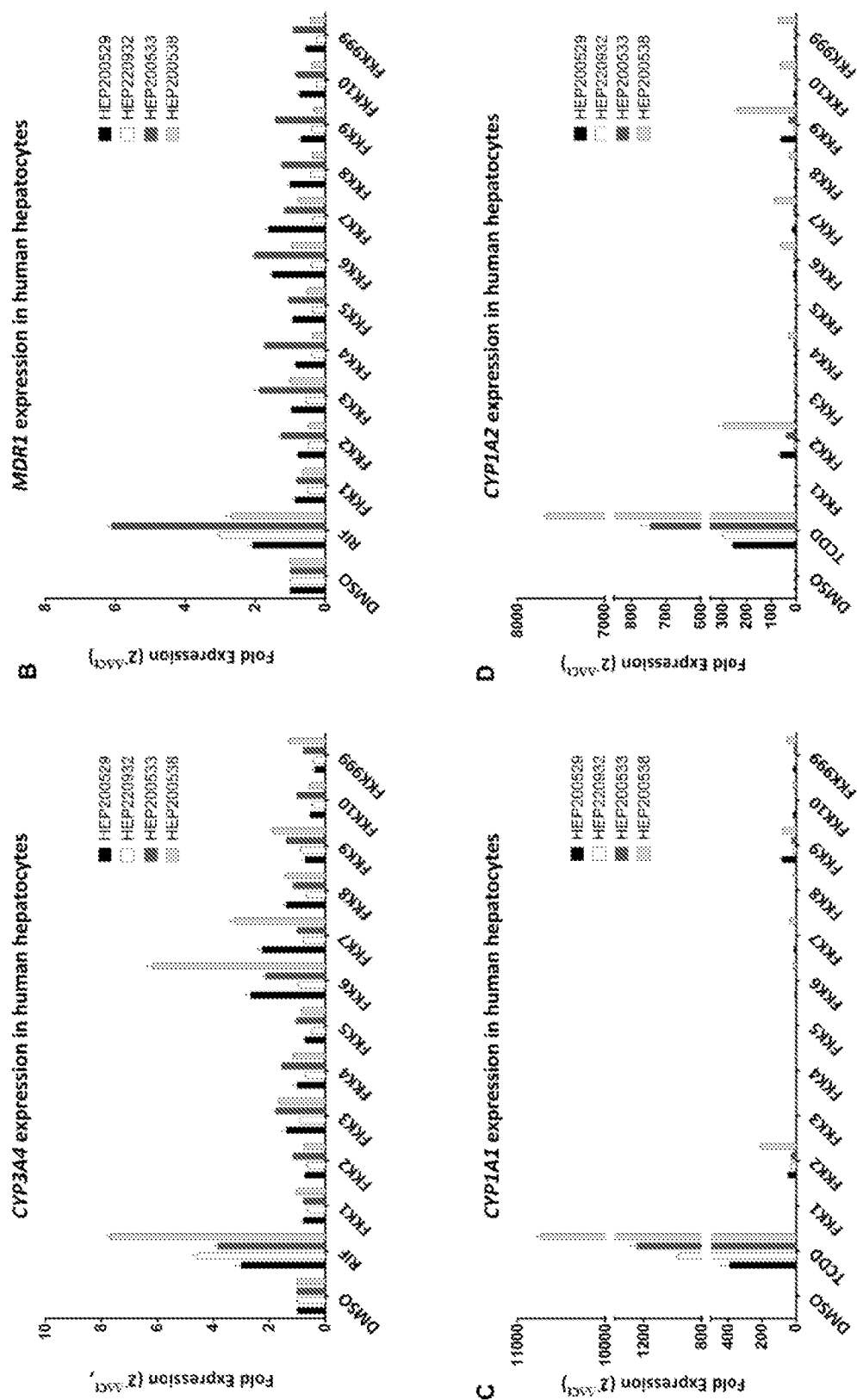
FIG. 8A-8D. Effects of FKK compounds on gene expression in human hepatocytes. (A) CYP3A4 expression. (B) MDR1 expression. (C) CYP1A1 expression. (D) CYP1A2 expression.
Figures 9A, 9B, 9C, 9D:
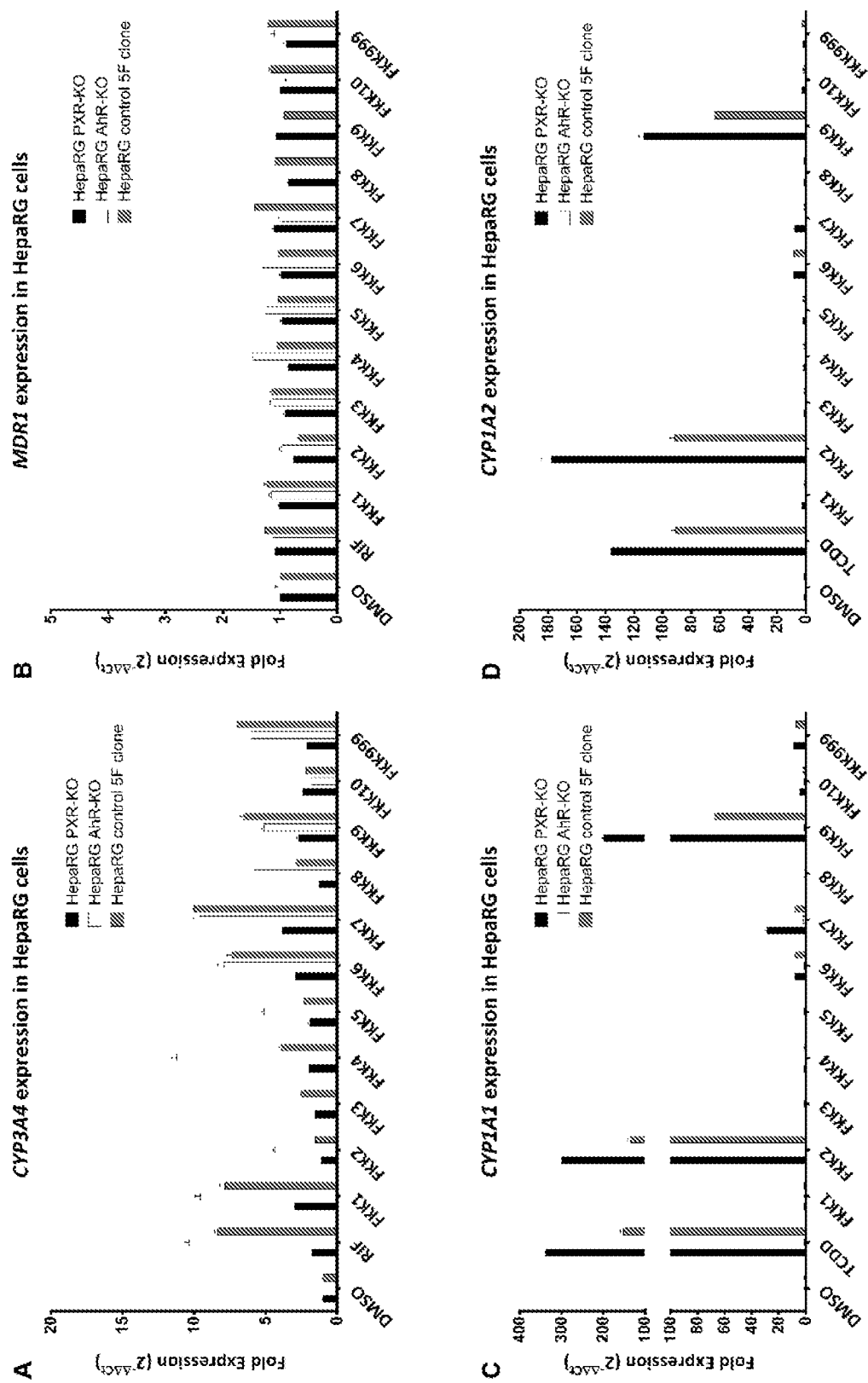
FIG. 9A-9D. Effects of FKK compounds on gene expression in HepaRG cells. (A) CYP3A4 expression. (B) MDR1 expression. (C) CYP1A1 expression. (D) CYP1A2 expression.

PXR agonists transcriptionally induce canonical target genes encoding drug metabolism enzymes/transporter, CYP3A4 and MDR1, in both liver (hepatocytes) (103) and intestinal cells (LS180) (104). HepaRG® cells simulate hepatocytes in that PXR ligands can also induce target genes in similar but not identical manner (105-107). AhR agonists transcriptionally induce target genes, CYP1A1 and CYP1A2, in both hepatocytes (102) and intestinal cells (LS180) (98). As shown in FIG. 7A, all compounds exhibited limited induction of CYP3A4 mRNA with FKK1 (1.4 fold) and FKK8 (1.5 fold) being borderline significant in un-transfected LS180 cells. By contrast, all compounds with the exception of FKK10, robustly enhanced MDR1 mRNA levels in these cells. Compounds FKK2 and 9, induced CYP1A1 mRNA expression (>100 fold) while other compounds FKK1, 3-6 and 999 had attenuated effects. To determine if PXR was indeed a contributing factor in gene expression, full-length human PXR transfected LS 180 cells were used to determine if the PXR target genes would be enhanced. As shown in FIG. 7B, there is significant enhancement of CYP3A4 mRNA by rifampicin (34.1 fold as compared to 2 fold, FIG. 7A). Similarly all the compounds except FKK10, resulted in significant induction of CYP3A4 mRNA. In comparison, there was a more modest but distinct increase in MDR1 mRNA levels. By contrast, the relative induction of CYP1A1 mRNA in PXR transfected LS180 cells were variably attenuated (TCDD 1299.1 fold; FKK2 272.5 fold; FKK9 388.9 fold) when compared to CYP1A1 expression in FIG. 6A (TCDD, 2347 fold; FKK2 822 fold; FKK9 814 fold). There is established cross-talk between PXR and AhR and it is conceivable that in LS180 cells (as in the case of hepatocytes) PXR could suppress AhR activation (108) and vice-versa (109); however, in both cell lines FKK2 and 9 induced CYP1A1 mRNA expression (>100 fold) while other compounds FKK1, 3-6 and 999 had attenuated effects. To determine the degree of PXR and AhR target gene induction in primary human plated hepatocytes, 4 distinct hepatocyte isolations were used. As shown in FIG. 8A, only compounds FKK6 and FKK7 had more than a 2 fold induction of CYP3A4 mRNA in 3 of 4 and 2 of 4 hepatocytes, respectively. Indeed, there was variation in expression across hepatocyte samples. The fold MDR1 mRNA induction was significantly attenuated with FKK6 being the only compound that exhibited ~2 fold induction in 1 of 4 hepatocyte specimens (FIG. 8B). In comparing the PXR target gene expression profile between primary hepatocytes (FIG. 8A-B) and LS180 cells (FIG. 7A-B), there is a qualitative robust induction of MDR1 mRNA in LS180 cells and not in hepatocytes; however, CYP3A4 mRNA is more robustly induced in hepatocytes than in LS180 cells. By contrast, AhR target genes (CYP1A1 and CYP1A2) were significantly induced by TCDD (>5000 fold) as compared to induction levels in LS180 cells (<3000 fold) (FIG. 7). Interestingly, there was variable induction (>100 fold) of CYP1A1 and CYP1A2 by compounds FKK2 and FKK9 in 1 of 4 hepatocytes, respectively. Finally, to verify whether PXR and/or AhR, is directly involved in the observed induction of CYP3A4, MDR1 and/or CYP1A1/CYP1A2, HepaRG® cells harboring loss of PXR or AhR. Target gene induction in these cell lines should be markedly diminished when compared to the wild type control cell line (110-111). Using both a N- and C-terminus antibody targeting PXR, the immunoblots show presence of a ~47-50 kDa band consistent with expression of PXR protein in HepaRG® PXR-KO cells; however, there is a clear loss of AhR protein in HepaRG® AhR-KO cells (data not shown). As shown in FIG. 9A, however, rifampicin does not induce CYP3A4 mRNA in HepaRG® PXR-KO cells as compared with HepaRG® control or HepaRG® AhR-KO cells. These data suggest that while HepaRG® PXR-KO cells retain PXR protein expression, it is non-functional. As shown further in FIG. 9A, all compounds (rifampicin, FKK 1, 3-9, and 999) induce CYP3A4 mRNA (>2 fold) in HepaRG® control cells and this expression is reduced in HepaRG® PXR-KO cells. By contrast, in FIG. 9B, none of the compounds, including rifampicin, induced MDR1 mRNA. In FIGS. 9C & 9D, FKK compounds 2 and 9, consistently induced CYP1A1 and CYP1A2, respectively (>100 fold), which was completely diminished in HepaRG® AhR-KO cells. The remaining compounds had variable to negligible effects on induction of AhR target genes. Interestingly, in a qualitative manner, the fold CYP1A1 and CYP1A2 gene induction in HepaRG® cells was consistently lower than that observed in primary hepatocytes (FIG. 8).

Kinase Profiling.

Figure 10:
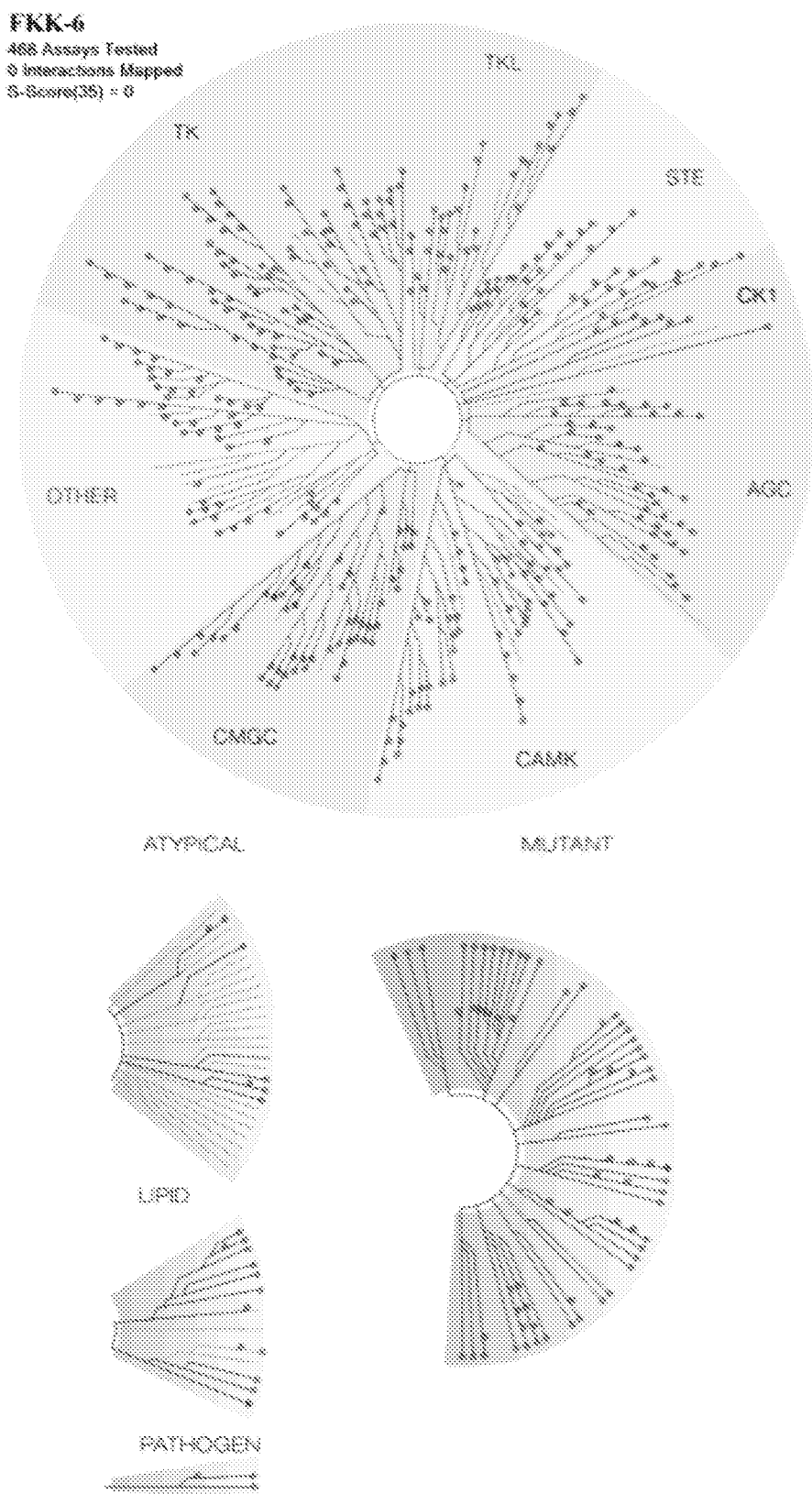
FIG. 10. TREEspot Kinase dendrogram image generated using TREEspot™ Software Tool indicating lack of inhibitory effects of compound FKK6 on any of 468 kinases.

The kinase inhibition assays were conducted by DiscoverX on a platform assay by Ambit BioSciences as described previously (112, 113). FKK6 was screened at a single concentration of 10 µM in duplicate. The scanMAXSM assay panel measures 468 kinases (WorldWideWeb.discoverx.com/services/drug-discovery-development-services/kinase-profiling/kinomescan/scanmax). The assays measures a compound's ability to inhibit binding of a canonical ligand substrate, with 0% activity of control corresponding to full inhibition and 100% activity of control to no inhibition. This data is then used to calculate a selectivity score (S-score), which is a quantitative measure of compound selectivity based on the number of kinase hits (enzymes inhibited) divided by the total number of distinct kinases tested. Three different activity cut-offs were analyzed—S(35) or % activity of control <35; S(10) or % activity of control <10; and S(1) or % activity of control <1. To illustrate effect or lack of effect, an image of the entire family of kinases tested were grouped by families and S(35). The TREEspot Kinase dendrogram image was generated using TREEspot™ Software Tool and reprinted with permission from KINOMEscan®, a division of DiscoveRx Corporation, © DISCOVERX CORPORATION 2010. The S(1-35)-scores for FKK6 were 0, suggesting lack of inhibitory effects of FKK6 on any kinase (Table 2; FIG. 10).

TABLE 2

S-Score results for compound FKK6.

| Selectivity Score Type | Number of Hits | Number of Non-Mutant Kinases | Screening Concentration (μM) | Selectivity Score (S-Score) |
|---|---|---|---|---|
| S(35) | 0 | 403 | 10 | 0 |
| S(10) | 0 | 403 | 10 | 0 |
| S(1) | 0 | 403 | 10 | 0 |

Chromatin Immunoprecipitation Assay (ChIP).

These assays were performed as previously published (27). As a representation, using semi-quantitative PCR, FKK6 efficiently induces PXR occupancy of the target promoters studied.

Isothermic Titration Calorimetry (ITC).

Figures 11A, 11B, 11C:
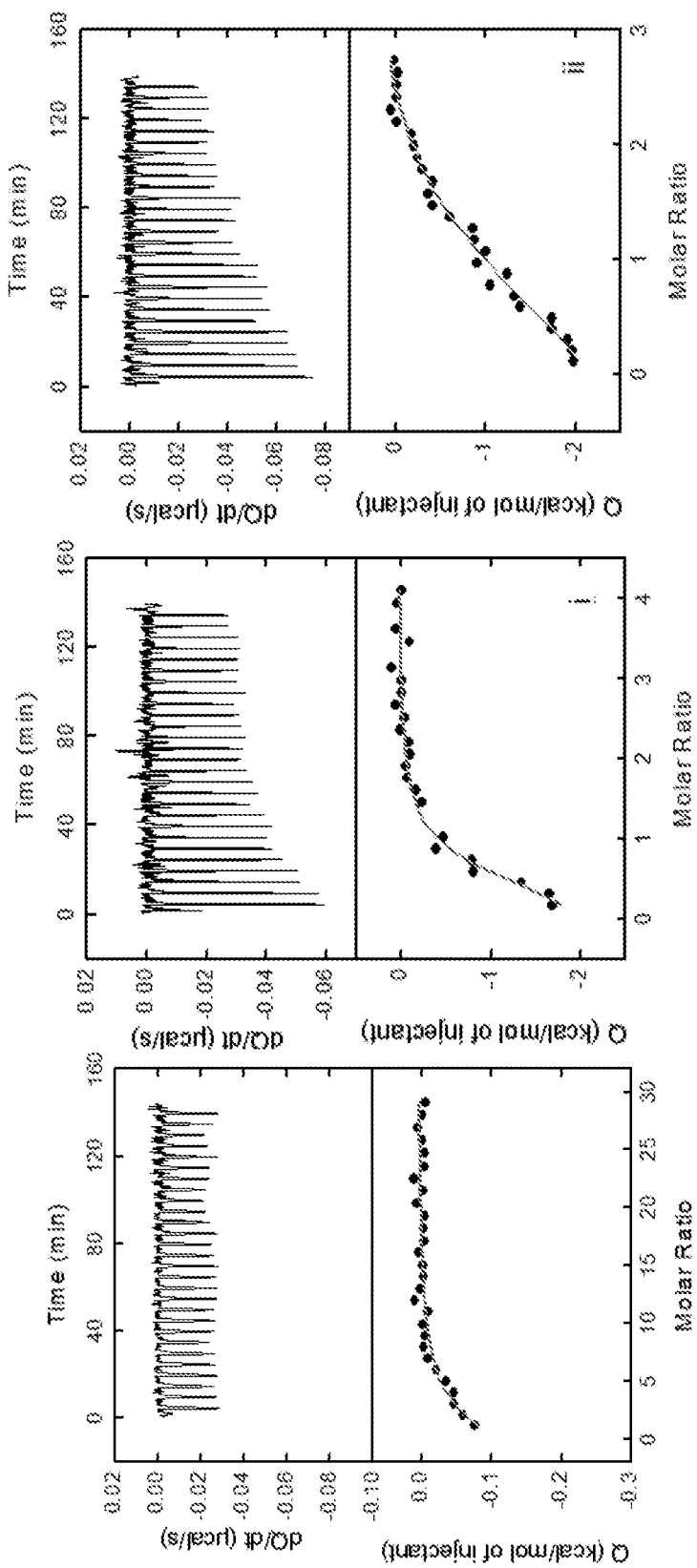
FIG. 11A-11C. Isothermic titration calorimetry studies showing efficient and direct binding of FKK5 (B) and FKK6 (C) indole3-propionic acid (IPA) (A) to human PXR.

These studies show efficient and direct binding of FKK5 (FIG. 11B) and FKK6 (FIG. 11C) but not IPA (indole3-propionic acid, FIG. 11A) to human PXR.

Human Intestinal Organoids.

Figure 12:
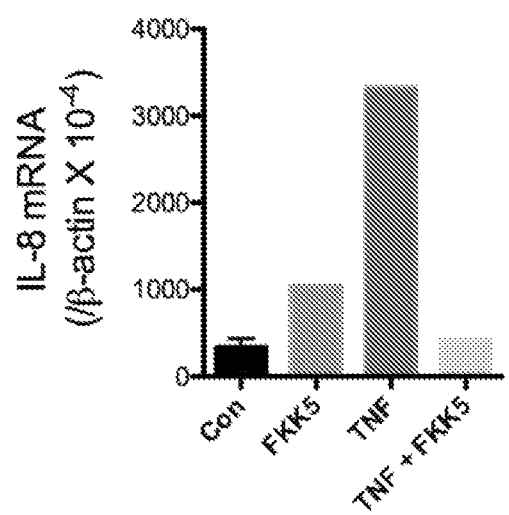
FIG. 12. Compound FKK5 reduces pro-inflammatory cytokine IL-8 expression induced by TNF in human intestinal organoids.

Intestinal organoids were developed using human small intestines and stem cell isolation and propagation in vitro. An initial (n=2) experiment indicates that there is a significant attenuation of TNF-induced IL-8 (a pro-inflammatory cytokine) by FKK5. The results show that FKK5 reduces pro-inflammatory cytokine expression during an inflammatory insult (e.g., TNF) (FIG. 12).

Mouse Studies.

In a mouse study, after in vivo delivery of 4 doses of 100 uM gavage over 3 days to humanized PXR C57BL/6 mice (n=3), there is a 2-fold induction of mdr1 in the small intestines but not in the colon or liver.

Docking Studies (all Compounds).

There is a clear relationship between high docking score cut-offs for PXR and PXR activation potential.

C1
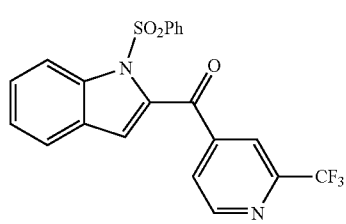
Log P = 3.86-5.61

C2
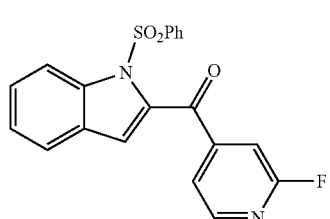
Log P = 3.53-4.87

C3
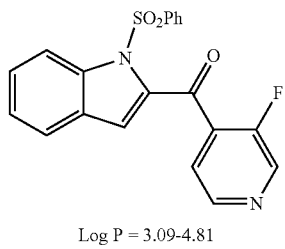
Log P = 3.09-4.81

C4
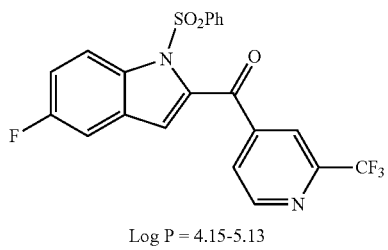
Log P = 4.15-5.13

C5
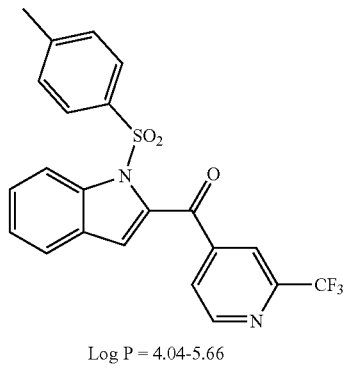
Log P = 4.04-5.66

C6
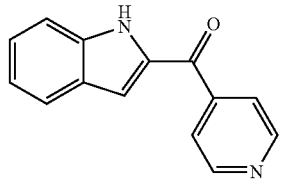
Log P = 2.52-3.29

C7
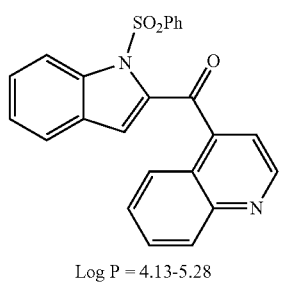
Log P = 4.13-5.28

-continued

C8

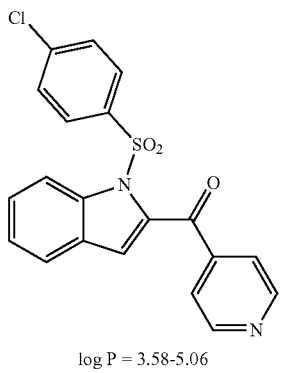

log P = 3.58-5.06

C9

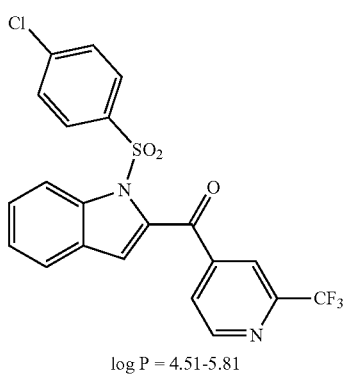

log P = 4.51-5.81

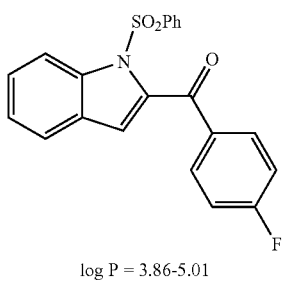

log P = 3.86-5.01

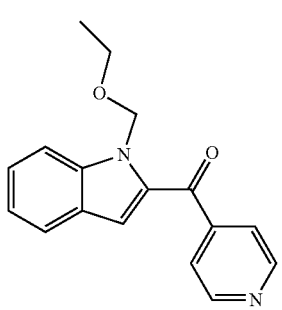

Log P = 2.52-3.77

The following results show direct high scores with either PXR and/or AhR:
C1=PXR
C2=PXR (AhR)
C3=PXR (AhR)
C4=PXR
C5=PXR
C6=PXR, AhR
C7=PXR (AhR)
C8=PXR (AhR)
C9=PXR C, 10=PXR (AhR)
C11=PXR (AhR).

TABLE 3

| Compound | LBP* | AF2 | α8 pocket |
|---|---|---|---|
| Compound 1 | 30.64 (29.87) | 22.49 (17.33) | 19.96 (11.54) |
| Compound 2 | 29.21 (24.52) | 22.21 (16.45) | 16.20 (8.35) |
| Compound 3 | 27.91 (25.57) | 16.79 (15.85) | 13.26 (6.44) |
| Compound 4 | 27.48 (29.10) | 20.35 (14.69) | 18.78 (11.68) |
| Compound 5 | 31.26 (30.92) | 21.79 (20.15) | 19.08 (10.04) |
| Compound 6 | 34.60 (32.88) | 23.45 (23.87) | 25.61 (16.84) |
| Compound 7 | 32.85 (37.70) | 24.64 (21.43) | 19.72 (10.94) |
| Compound 8 | 31.45 (28.85) | 17.80 (16.46) | 20.05 (9.32) |
| Compound 9 | 31.06 (29.67) | 22.39 (21.35) | 22.34 (12.67) |
| Compound 10 | 33.05 (32.50) | 20.68 (20.04) | 19.23 (10.95) |
| Compound 11 | 31.99 (29.24) | 24.05 (21.71) | 23.06 (15.82) |
| FK5 | 37.16 (34.65) | 26.47 (20.90) | 26.21 (20.24) |
| Blue_1 | 34.77 (30.68) | 22.44 (24.16) | 25.62 (15.54) |
| Blue_2 | 33.63 (31.17) | 24.46 (21.12) | 20.71 (15.45) |
| Blue_3 | 34.65 (30.89) | 22.41 (23.58) | 18.73 (10.98) |
| FK6 | 30.42 (27.13) | 20.92 (17.89) | 16.13 (8.70) |

Compounds simulated for structural variations of these (and presented in the chemical schematic) all show high PXR docking scores. In a separate docking analysis of compounds presented below (*Score obtained with PDBID 1NRL are in parenthesis). The AF2 and α8 pockets are antagonist pockets.

C10

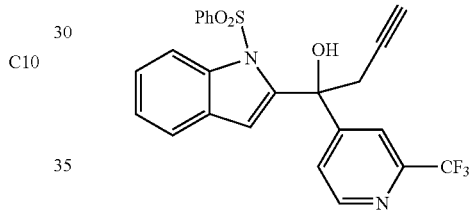

Log P = 3.79-5.12

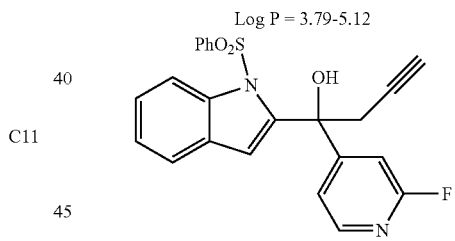

Log P = 2.85-4.72

C11

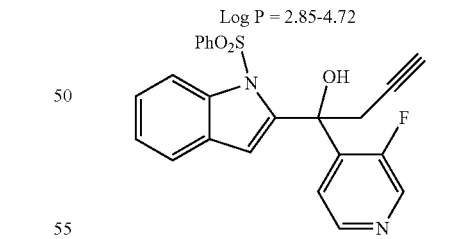

Log P = 2.31-4.71

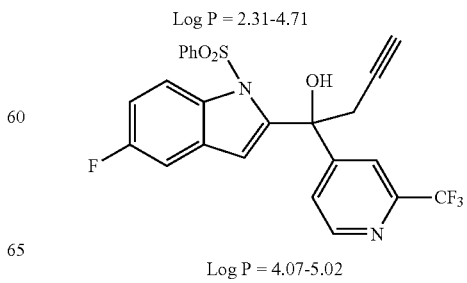

Log P = 4.07-5.02

33
-continued
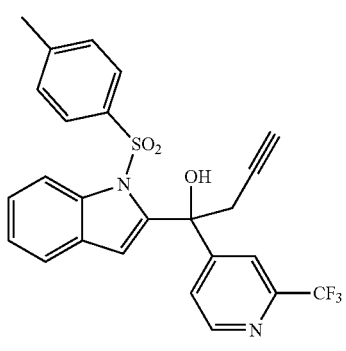
Log P = 3.97-5.16
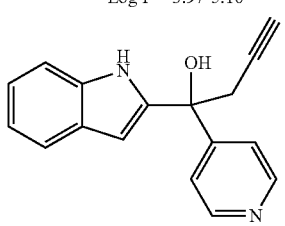
Log P = 2.56-4.40
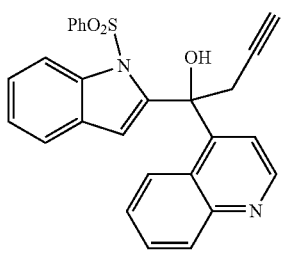
Log P = 3.87-5.07
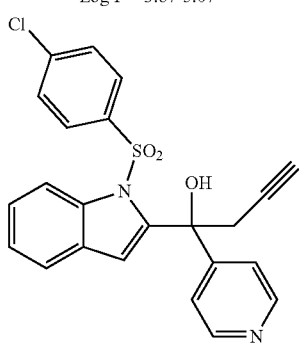
log P = 3.06-4.86
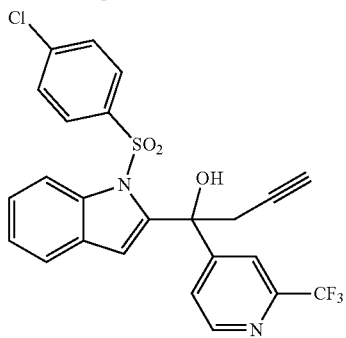
log P = 4.35-5.22
34
-continued
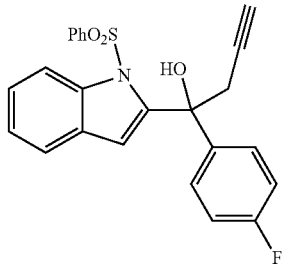
log P = 3.69-4.92
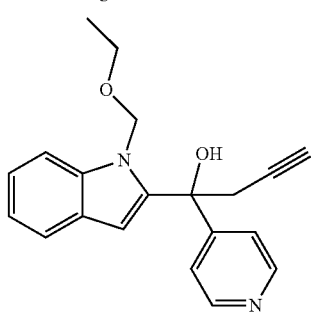
Log P = 2.80-4.21
From left to right, Compound 1 though Compound 11.
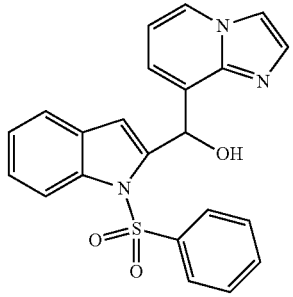
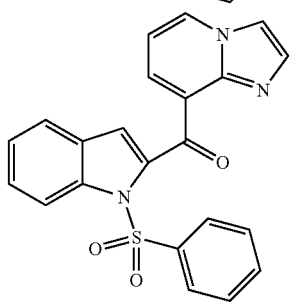
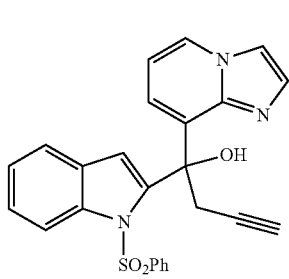
From left to right, compounds Blue 1, Blue 2 and Blue 3.

REFERENCES

1. Kaser A., S. Zeissig, R. S. Blumberg, *Annu Rev Immunol* 28, 573 (2010).
2. Turner J. R., *Nat Rev Immunol* 9, 799 (2009).
3. Krack A., R. Sharma, H. R. Figulla, S. D. Anker, *Eur Heart J* 26, 2368 (2005).
4. Vaarala O., *Curr Opin Gastroenterol* 24, 701 (2008).
5. Liu Z., N. Li, J. Neu, *Acta Paediatr* 94, 386 (2005).
6. Chawla, A., Repa, J. J., Evans, R. M., and Mangelsdorf, D. J. (2001) Nuclear receptors and lipid physiology: opening the X-files. Science 294, 1866-70.
7. Gronemeyer, H., Gustafsson, J. A., and Laudet, V. (2004) Principles for modulation of the nuclear receptor superfamily. Nat Rev Drug Discov 3, 950-64.
8. Mangelsdorf, D. J., and Evans, R. M. (1995) The RXR heterodimers and orphan receptors. Cell 83, 841-50.
9. Mangelsdorf, D. J., Thummel, C., Beato, M., Herrlich, P., Schutz, G., Umesono, K., Blumberg, B., Kastner, P., Mark, M., Chambon, P., and et al. (1995) The nuclear receptor superfamily: the second decade. Cell 83, 835-9.
10. Ingraham, H. A., and Redinbo, M. R. (2005) Orphan nuclear receptors adopted by crystallography. *Curr Opin Struct Biol* 15, 708-15.
11. McDonnell, D. P., Connor, C. E., Wijayaratne, A., Chang, C. Y., and Norris, J. D.
(2002) Definition of the molecular and cellular mechanisms underlying the tissue-selective agonist/antagonist activities of selective estrogen receptor modulators. Recent Prog Horm Res 57, 295-316.
12. Shiau, A. K., Barstad, D., Loria, P. M., Cheng, L., Kushner, P. J., Agard, D. A., and Greene, G. L. (1998) The structural basis of estrogen receptor/coactivator recognition and the antagonism of this interaction by tamoxifen. Cell 95, 927-937.
13. Kliewer, S. A., Moore, J. T., Wade, L., Staudinger, J. L., Watson, M. A., Jones, S. A., McKee, D. D., Oliver, B. B., Willson, T. M., Zetterstrom, R. H., Perlmann, T., and Lehmann, J. M. (1998) An orphan nuclear receptor activated by pregnanes defines a novel steroid signaling pathway. Cell 92, 73-82.
14. Fayard, E., Auwerx, J., and Schoonjans, K. (2004) LRH-1: an orphan nuclear receptor involved in development, metabolism and steroidogenesis. Trends Cell Biol 14, 250-60.
15. Bertilsson, G., Heidrich, J., Svensson, K., Asman, M., Jendeberg, L., Sydow-Backman, M., Ohlsson, R., Postlind, H., Blomquist, P., and Berkenstam, A. (1998) Identification of a human nuclear receptor defines a new signaling pathway for CYP3A induction. Proceedings of the National Academy of Sciences of the United States of America 95, 12208-13.
16. Mani S, Huang H, Sundarababu S, et al. Activation of the steroid and xenobiotic receptor (human pregnane X receptor) by nontaxane microtubule-stabilizing agents. Clin Cancer Res. 2005 Sep. 1; 11(17):6359-69.
17. Pascual, G. & Glass, C. K. Nuclear receptors versus inflammation: mechanisms of transrepression. *Trends Endocrinol. Metab* 17, 321-327 (2006).
18. Huang, W. & Glass, C. K. Nuclear receptors and inflammation control: molecular mechanisms and pathophysiological relevance. *Arterioscler Thromb Vasc Biol* 30, 1542-1549 (2010).
19. Saijo, K., Crotti, A. & Glass, C. K. Nuclear receptors, inflammation, and neurodegenerative diseases. *Adv. Immunol* 106, 21-59 (2010).
20. Harmon, G. S., Lam, M. T. & Glass, C. K. PPARs and lipid ligands in inflammation and metabolism. *Chem. Rev* 111, 6321-6340 (2011).
21. Pascual, G., et al. Anti-inflammatory and antidiabetic roles of PPARgamma. *Novartis. Found. Symp* 286, 183-196 (2007).
22. Ma, X., Idle, J. R. & Gonzalez, F. J. The pregnane X receptor: from bench to bedside. *Expert. Opin. Drug Metab Toxicol* 4, 895-908 (2008).
23. Ma, X., et al. Rifaximin is a gut-specific human pregnane X receptor activator. *J Pharmacol Exp Ther* 322, 391-398 (2007).
24. Shah, Y. M., Ma, X., Morimura, K., Kim, I. & Gonzalez, F. J. Pregnane X receptor activation ameliorates DSS-induced inflammatory bowel disease via inhibition of NF-kappaB target gene expression. *Am. J. Physiol Gastrointest. Liver Physiol* 292, G1114-G1122 (2007).
25. Cheng, J., Shah, Y. M. & Gonzalez, F. J. Pregnane X receptor as a target for treatment of inflammatory bowel disorders. *Trends Pharmacol Sci* 33, 323-330 (2012).
26. Cheng, J., et al. Activation of intestinal human pregnane X receptor protects against azoxymethane/dextran sulfate sodium-induced colon cancer. *J Pharmacol Exp Ther* 351, 559-567 (2014).
27. Dou, W., et al. Alleviation of gut inflammation by Cdx2/Pxr pathway in a mouse model of chemical colitis. *PLoS One* 7, e36075 (2012).
28. Dou, W., et al. Plant flavonol isorhamnetin attenuates chemically induced inflammatory bowel disease via a PXR-dependent pathway. *J Nutr Biochem* 25, 923-933 (2014).
29. Dou, W., et al. Chrysin ameliorates chemically induced colitis in the mouse through modulation of a PXR/NF-kappaB signaling pathway. *J Pharmacol Exp Ther* 345, 473-482 (2013).
30. Hu, D., et al. The protective effect of piperine on dextran sulfate sodium induced inflammatory bowel disease and its relation with pregnane X receptor activation. *J Ethnopharmacol* 169, 109-123 (2015).
31. Hu, D., et al. Artemisinin protects against dextran sulfate-sodium-induced inflammatory bowel disease, which is associated with activation of the pregnane X receptor. *European journal of pharmacology* 738, 273-284 (2014).
32. Sepe, V., et al. Total synthesis and pharmacological characterization of solomonsterol A, a potent marine pregnane-X-receptor agonist endowed with anti-inflammatory activity. *J Med Chem* 54, 4590-4599 (2011).
33. Venkatesh, M., et al. Symbiotic bacterial metabolites regulate gastrointestinal barrier function via the xenobiotic sensor PXR and Toll-like receptor 4. *Immunity* 41, 296-310 (2014).
34. Ye, N., et al. PXR Mediated Protection against Liver Inflammation by Ginkgolide A in Tetrachloromethane Treated Mice. *Biomol Ther (Seoul)* 24, 40-48 (2016).
35. Zhang, J., et al. Notoginsenoside R1 attenuates experimental inflammatory bowel disease via pregnane X receptor activation. *J Pharmacol Exp Ther* 352, 315-324 (2015).
36. Zhang, X., et al. Tanshinone IIA ameliorates dextran sulfate sodium-induced inflammatory bowel disease via the pregnane X receptor. *Drug Des Devel Ther* 9, 6343-6362 (2015).
37. Zhou, C., et al. Mutual repression between steroid and xenobiotic receptor and NF-kappaB signaling pathways links xenobiotic metabolism and inflammation. *J Clin Invest* 116, 2280-2289 (2006).

38. Shakhnovich, V., et al. Decreased Pregnane X Receptor Expression in Children with Active Crohn's Disease. *Drug Metab Dispos* 44, 1066-1069 (2016).
39. Blokzijl, H., et al. Decreased P-glycoprotein (P-gp/MDR1) expression in inflamed human intestinal epithelium is independent of PXR protein levels. *Inflamm Bowel Dis* 13, 710-720 (2007).
40. Langmann, T., et al. Loss of detoxification in inflammatory bowel disease: dysregulation of pregnane X receptor target genes. *Gastroenterology* 127, 26-40 (2004).
41. Amre, D. K., et al. Investigation of associations between the pregnane-X receptor gene (NR1I2) and Crohn's disease in Canadian children using a gene-wide haplotype-based approach. *Inflamm Bowel Dis* 14, 1214-1218 (2008).
42. Dring, M. M., et al. The pregnane X receptor locus is associated with susceptibility to inflammatory bowel disease. *Gastroenterology* 130, 341-348; quiz 592 (2006).
43. Glas, J., et al. Pregnane X receptor (PXR/NR1I2) gene haplotypes modulate susceptibility to inflammatory bowel disease. *Inflamm Bowel Dis* 17, 1917-1924 (2011).
44. Ho, G. T., et al. Lack of association of the pregnane X receptor (PXR/NR1I2) gene with inflammatory bowel disease: parallel allelic association study and gene wide haplotype analysis. *Gut* 55, 1676-1677 (2006).
45. Martinez, A., et al. Role of the PXR gene locus in inflammatory bowel diseases. *Inflamm Bowel Dis* 13, 1484-1487 (2007).
46. Wang, Y. M., Ong, S. S., Chai, S. C. & Chen, T. Role of CAR and PXR in xenobiotic sensing and metabolism. *Expert opinion on drug metabolism & toxicology* 8, 803-817 (2012).
47. Bajaj, J. S., et al. Modulation of the metabiome by rifaximin in patients with cirrhosis and minimal hepatic encephalopathy. *PLoS One* 8, e60042 (2013).
48. Cheng, J., Krausz, K. W., Tanaka, N. & Gonzalez, F. J. Chronic exposure to rifaximin causes hepatic steatosis in pregnane X receptor-humanized mice. *Toxicol. Sci* 129, 456-468 (2012).
49. Sartor, R. B. Review article: the potential mechanisms of action of rifaximin in the management of inflammatory bowel diseases. *Aliment Pharmacol Ther* 43 Suppl 1, 27-36 (2016).
50. Hirota, S. A. Understanding the Molecular Mechanisms of Rifaximin in the Treatment of Gastrointestinal Disorders—A Focus on the Modulation of Host Tissue Function. *Mini Rev Med Chem* 16, 206-217 (2015).
51. Mitro, N., Vargas, L., Romeo, R., Koder, A. & Saez, E. T0901317 is a potent PXR ligand: implications for the biology ascribed to LXR. *FEBS Lett* 581, 1721-1726 (2007).
52. Chisholm, J. W., Hong, J., Mills, S. A. & Lawn, R. M. The LXR ligand T0901317 induces severe lipogenesis in the db/db diabetic mouse. *J Lipid Res* 44, 2039-2048 (2003).
53. Kothary, V., et al. Rifaximin resistance in *Escherichia coli* associated with inflammatory bowel disease correlates with prior rifaximin use, mutations in rpoB, and activity of Phe-Arg-beta-naphthylamide-inhibitable efflux pumps. *Antimicrob Agents Chemother* 57, 811-817 (2013).
54. Gramec Skledar, D., et al. New brominated flame retardants and their metabolites as activators of the pregnane X receptor. *Toxicol Lett* 259, 116-123 (2016).
55. Laurenzana, E. M., Coslo, D. M., Vigilar, M. V., Roman, A. M. & Omiecinski, C. J. Activation of the Constitutive Androstane Receptor by Monophthalates. *Chem Res Toxicol* (2016).
56. Hurst, C. H. & Waxman, D. J. Environmental phthalate monoesters activate pregnane X receptor-mediated transcription. *Toxicol Appl Pharmacol* 199, 266-274 (2004).
57. Maitre, T., Aubry, A., Jarlier, V., Robert, J. & Veziris, N. Multidrug and extensively drug-resistant tuberculosis. *Med Mal Infect* (2016).
58. Watkins R E, Wisely G B, Moore L B, Collins J L, Lambert M H, Williams S P, Willson T M, Kliewer S A, Redinbo M R. The human nuclear xenobiotic receptor PXR: structural determinants of directed promiscuity. Science. 2001; 292(5525):2329-33.
59. Chrencik J E, Orans J, Moore L B, Xue Y, Peng L, Collins J L, Wisely G B, Lambert M H, Kliewer S A, Redinbo M R. Structural disorder in the complex of human pregnane X receptor and the macrolide antibiotic rifampicin. Mol Endocrinol. 2005; 19(5):1125-34.
60. Kamenickova A, Pecova M, Bachleda P, Dvorak Z. Effects of artificial sweeteners on the AhR- and GR-dependent CYP1A1 expression in primary human hepatocytes and human cancer cells. Toxicol In Vitro. 2013; 27(8):2283-8. Epub 2013 Oct. 15.
61. Korhonova M, Doricakova A, Dvorak Z. Optical Isomers of Atorvastatin, Rosuvastatin and Fluvastatin Enantiospecifically Activate Pregnane X Receptor PXR and Induce CYP2A6, CYP2B6 and CYP3A4 in Human Hepatocytes. PLoS One. 2015; 10(9):e0137720. Epub 2015 Sep. 15.
62. Kubesova K, Travnicek Z, Dvorak Z. Pleiotropic effects of gold(I) mixed-ligand complexes of 9-deazahypoxanthine on transcriptional activity of receptors for steroid hormones, nuclear receptors and xenoreceptors in human hepatocytes and cell lines. Eur J Med Chem. 2016; 121:530-40. Epub 2016 Jun. 20.
63. Novotna A, Doricakova A, Pavek P, Dvorak Z. Construction and characterization of peroxisome proliferator-activated receptor-gamma co-activator 1 alpha (PGC-1alpha over-expressing cell line derived from human hepatocyte carcinoma HepG2 cells). Biomed Pap Med Fac Univ Palacky Olomouc Czech Repub. 2013; 157(3): 214-21. Epub 2012 Oct. 18.
64. Novotna A, Dvorak Z. Omeprazole and lansoprazole enantiomers induce CYP3A4 in human hepatocytes and cell lines via glucocorticoid receptor and pregnane X receptor axis. *PLoS One.* 2014; 9(8):e105580. Epub 2014 Aug. 21.
65. Novotna A, Kamenickova A, Pecova M, Korhonova M, Bartonkova I, Dvorak Z. Profiling of enantiopure drugs towards aryl hydrocarbon (AhR), glucocorticoid (GR) and pregnane X (PXR) receptors in human reporter cell lines. Chem Biol Interact. 2014; 208:64-76. Epub 2013 Dec. 10.
66. Novotna A, Krasulova K, Bartonkova I, Korhonova M, Bachleda P, Anzenbacher P, Dvorak Z. Dual effects of ketoconazole cis-enantiomers on CYP3A4 in human hepatocytes and HepG2 Cells. PLoS One. 2014; 9(10): e111286. Epub 2014 Oct. 25.
67. Pasquel D, Doricakova A, Li H, Kortagere S, Krasowski M D, Biswas A, Walton W G, Redinbo M R, Dvorak Z, Mani S. Acetylation of lysine 109 modulates pregnane X receptor DNA binding and transcriptional activity. Biochim Biophys Acta. 2016; 1859(9):1155-69. Epub 2016 Feb. 9.

68. Smutny T, Bitman M, Urban M, Dubecka M, Vrzal R, Dvorak Z, Pavek P. U0126, a mitogen-activated protein kinase 1 and 2 (MEK1 and 2) inhibitor, selectively up-regulates main isoforms of CYP3A subfamily via a pregnane X receptor (PXR) in HepG2 cells. Arch Toxicol. 2014; 88(12):2243-59. Epub 2014 May 14.
69. Vavrova A, Vrzal R, Dvorak Z. A nonradioactive electrophoretic mobility shift assay for measurement of pregnane X receptor binding activity to CYP3A4 response element. Electrophoresis. 2013; 34(13): 1863-8. Epub 2013 Aug. 27.
70. Vrzal R, Dvorak Z. The comparative effects of diethyldithiocarbamate-copper complex with established proteasome inhibitors on expression levels of CYP1A2/3A4 and their master regulators, aryl hydrocarbon and pregnane X receptor in primary cultures of human hepatocytes. Fundam Clin Pharmacol. 2016. Epub 2016 Jul. 15.
71. Vrzal R, Zenata O, Doricakova A, Dvorak Z. Environmental pollutants parathion, paraquat and bisphenol A show distinct effects towards nuclear receptors-mediated induction of xenobiotics-metabolizing cytochromes P450 in human hepatocytes. Toxicol Lett. 2015; 238(1):43-53. Epub 2015 Jul. 22.
72. Jones B C, Rollison H, Johansson S A, Kanebratt K P, Lambert C, Vishwanathan K, Andersson T B. Managing the Risk of CYP3A Induction in Drug Development: A Strategic Approach. Drug metabolism and disposition: the biological fate of chemicals. 2016. Epub 2016 Oct. 26.
73. Terc, J., Hansen, A., Alston, L. & Hirota, S. A. Pregnane X receptor agonists enhance intestinal epithelial wound healing and repair of the intestinal barrier following the induction of experimental colitis. *European journal of pharmaceutical sciences: official journal of the European Federation for Pharmaceutical Sciences* 55, 12-19 (2014).
74. Ila, H.; Markiewicz, J. T.; Malakhov, V.; Knochel, P. *Synthesis* 2013, 45, 2343-2371.
75. Klatt, T.; Markiewicz, J. T.; Saemann, C.; Knochel, P. *J. Org. Chem.* 2014, 79, 4253-4269.
76. Knochel, P.; Schade, M. A.; Bernhardt, S.; Manolikakes, G.; Metzger, A.; Piller, F. M.; Rohbogner, C. J.; Mosrin, M. *Beilstein J Org. Chem.* 2011, 7, 1261-1277.
77. Knochel, P.; Dohle, W.; Gommermann, N.; Kneisel, F. F.; Kopp, F.; Korn, T.; Sapountzis, I.; Vu, V. A. *Angew. Chem. Int. Ed.* 2003, 42, 4302-4320.
78. Ren A, Su B, Ye S, Wei X, Fang Z, Wang Q, Zhang J, Xu W, Yue W, Yin L, Liu Z, Li X, Ding B O. A pharmacokinetic study of Isatin in Beagles' bodies. Exp Ther Med. 2016; 11(6):2225-8. Epub 2016 Jun. 11.
79. Li M, Meng X, Xu J, Huang X, Li H, Li G, Wang S, Man Y, Tang W, Li J. GPR40 agonist ameliorates liver X receptor-induced lipid accumulation in liver by activating AMPK pathway. Sci Rep. 2016; 6:25237. Epub 2016 Apr. 29.
80. Dong B, Lee J S, Park Y Y, Yang F, Xu G, Huang W, Finegold M J, Moore D D. Activating CAR and beta-catenin induces uncontrolled liver growth and tumorigenesis. Nat Commun. 2015; 6:5944. Epub 2015 Feb. 11.
81. Hubbard T D, Murray I A, Bisson W H, Lahoti T S, Gowda K, Amin S G, Patterson A D, Perdew G H. Adaptation of the human aryl hydrocarbon receptor to sense microbiota-derived indoles. Scientific reports. 2015; 5:12689. Epub 2015 Aug. 4. doi: 10.1038/srep12689.
82. Jin U H, Lee S O, Sridharan G, Lee K, Davidson L A, Jayaraman A, Chapkin R S, Alaniz R, Safe S. Microbiome-derived tryptophan metabolites and their aryl hydrocarbon receptor-dependent agonist and antagonist activities. Mol Pharmacol. 2014; 85(5):777-88. Epub 2014 Feb. 25.
83. Cave M C, Clair H B, Hardesty J E, Falkner K C, Feng W, Clark B J, Sidey J, Shi H, Aqel B A, McClain C J, Prough R A. Nuclear receptors and nonalcoholic fatty liver disease. Biochim Biophys Acta. 2016; 1859(9): 1083-99. Epub 2016 Mar. 11.
84. Marmugi A, Lukowicz C, Lasserre F, Montagner A, Polizzi A, Ducheix S, Goron A, Gamet-Payrastre L, Gerbal-Chaloin S, Pascussi J M, Moldes M, Pineau T, Guillou H, Mselli-Lakhal L. Activation of the Constitutive Androstane Receptor induces hepatic lipogenesis and regulates Pnpla3 gene expression in a LXR-independent way. Toxicol Appl Pharmacol. 2016; 303:90-100.
85. Sim W C, Kim D G, Lee K J, Choi Y J, Choi Y J, Shin K J, Jun D W, Park S J, Park H J, Kim J, Oh W K, Lee B H. Cinnamamides, Novel Liver X Receptor Antagonists that Inhibit Ligand-Induced Lipogenesis and Fatty Liver. J Pharmacol Exp Ther. 2015; 355(3):362-9. Epub 2015 Sep. 20.
86. Oh G S, Yoon J, Lee G G, Oh W K, Kim S W. 20(S)-protopanaxatriol inhibits liver X receptor alpha-mediated expression of lipogenic genes in hepatocytes. J Pharmacol Sci. 2015; 128(2):71-7. Epub 2015 Jun. 26.
87. Rouquie D, Tinwell H, Blanck O, Schorsch F, Geter D, Wason S, Bars R. Thyroid tumor formation in the male mouse induced by fluopyram is mediated by activation of hepatic CAR/PXR nuclear receptors. Regulatory toxicology and pharmacology: RTP. 2014; 70(3):673-80. Epub 2014 Dec. 3.
88. Tamura K, Inoue K, Takahashi M, Matsuo S, Irie K, Kodama Y, Gamo T, Ozawa S, Yoshida M. Involvement of constitutive androstane receptor in liver hypertrophy and liver tumor development induced by triazole fungicides. Food Chem Toxicol. 2015; 78:86-95. Epub 2015/02/07.
89. Yueh M F, Taniguchi K, Chen S, Evans R M, Hammock B D, Karin M, Tukey R H. The commonly used antimicrobial additive triclosan is a liver tumor promoter. Proc Natl Acad Sci USA. 2014; 111(48):17200-5. Epub 2014 Nov. 19.
90. Mackowiak B, Wang H. Mechanisms of xenobiotic receptor activation: Direct vs. indirect. Biochim Biophys Acta. 2016; 1859(9):1130-40. Epub 2016 Feb. 16.
91. Huang, H. et al. Inhibition of drug metabolism by blocking the activation of nuclear receptors by ketoconazole. *Oncogene* 26, 258-268, doi:10.1038/sj.onc.1209788 (2007).
92. Goodwin, B., Hodgson, E. & Liddle, C. The orphan human pregnane X receptor mediates the transcriptional activation of CYP3A4 by rifampicin through a distal enhancer module. *Molecular pharmacology* 56, 1329-1339 (1999).
93. Novotna, A., Pavek, P. & Dvorak, Z. Novel stably transfected gene reporter human hepatoma cell line for assessment of aryl hydrocarbon receptor transcriptional activity: construction and characterization. *Environmental science & technology* 45, 10133-10139, doi:10.1021/es2029334 (2011).
94. Bartonkova, I., Grycova, A. & Dvorak, Z. Profiling of Vitamin D Metabolic Intermediates toward VDR Using Novel Stable Gene Reporter Cell Lines IZ-VDRE and IZ-CYP24. *Chemical research in toxicology* 29, 1211-1222, doi: 10.1021/acs.chemrestox.6b00170 (2016).
95. Bartonkova, I., Novotna, A. & Dvorak, Z. Novel stably transfected human reporter cell line AIZ-AR as a tool for 96. Illes, P., Brtko, J. & Dvorak, Z. Development and Characterization of a Human Reporter Cell Line for the Assessment of Thyroid Receptor Transcriptional Activity: A Case of Organotin Endocrine Disruptors. *Journal of agricultural and food chemistry* 63, 7074-7083, doi: 10.1021/acs.jafc.5b01519 (2015).
97. Krausova, L. et al. Metformin suppresses pregnane X receptor (PXR)-regulated transactivation of CYP3A4 gene. *Biochemical pharmacology* 82, 1771-1780, doi: 10.1016/j.bcp.2011.08.023 (2011).
98. Kubesova, K., Doricakova, A., Travnicek, Z. & Dvorak, Z. Mixed-ligand copper(II) complexes activate aryl hydrocarbon receptor AhR and induce CYP1A genes expression in human hepatocytes and human cell lines. *Toxicology letters* 255, 24-35, doi:10.1016/j.toxlet.2016.05.014 (2016).
99. Li, H., Dou, W., Padikkala, E. & Mani, S. Reverse yeast two-hybrid system to identify mammalian nuclear receptor residues that interact with ligands and/or antagonists. *Journal of visualized experiments: JoVE*, e51085, doi: 10.3791/51085 (2013).
100. Monostory, K., Pascussi, J. M., Kobori, L. & Dvorak, Z. Hormonal regulation of CYP1A expression. *Drug metabolism reviews* 41, 547-572, doi: 10.1080/03602530903112284 (2009).
101. Novotna, A., Pavek, P. & Dvorak, Z. Construction and characterization of a reporter gene cell line for assessment of human glucocorticoid receptor activation. *European journal of pharmaceutical sciences: official journal of the European Federation for Pharmaceutical Sciences* 47, 842-847, doi:10.1016/j.ejps.2012.10.003 (2012).
102. Pastorkova, B., Vrzalova, A., Bachleda, P. & Dvorak, Z. Hydroxystilbenes and methoxystilbenes activate human aryl hydrocarbon receptor and induce CYP1A genes in human hepatoma cells and human hepatocytes. *Food Chem Toxicol* 103, 122-132, doi: 10.1016/j.fct.2017.03.008 (2017).
103. Kandel, B. A. et al. Genomewide comparison of the inducible transcriptomes of nuclear receptors CAR, PXR and PPARalpha in primary human hepatocytes. *Biochimica et biophysica acta* 1859, 1218-1227, doi: 10.1016/j.bbagrm.2016.03.007 (2016).
104. Gupta, A., Mugundu, G. M., Desai, P. B., Thummel, K. E. & Unadkat, J. D. Intestinal human colon adenocarcinoma cell line LS180 is an excellent model to study pregnane X receptor, but not constitutive androstane receptor, mediated CYP3A4 and multidrug resistance transporter 1 induction: studies with anti-human immunodeficiency virus protease inhibitors. *Drug metabolism and disposition: the biological fate of chemicals* 36, 1172-1180, doi:10.1124/dmd.107.018689 (2008).
105. Aninat, C. et al. Expression of cytochromes P450, conjugating enzymes and nuclear receptors in human hepatoma HepaRG cells. *Drug metabolism and disposition: the biological fate of chemicals* 34, 75-83, doi: 10.1124/dmd.105.006759 (2006).
106. Andersson, T. B. The application of HepRG cells in evaluation of cytochrome P450 induction properties of drug compounds. *Methods in molecular biology (Clifton, N.J.)* 640, 375-387, doi: 10.1007/978-1-60761-688-7_20 (2010).
107. Antherieu, S., Chesne, C., Li, R., Guguen-Guillouzo, C. & Guillouzo, A. Optimization of the HepaRG cell model for drug metabolism and toxicity studies. *Toxicology in vitro: an international journal published in association with BIBRA* 26, 1278-1285, doi:10.1016/j.tiv.2012.05.008 (2012).
108. Cui, H. et al. Pregnane X receptor regulates the AhR/Cyp1A1 pathway and protects liver cells from benzo-[alpha]-pyrene-induced DNA damage. *Toxicology letters* 275, 67-76, doi:10.1016/j.toxlet.2017.03.028 (2017).
109. Rasmussen, M. K., Daujat-Chavanieu, M. & Gerbal-Chaloin, S. Activation of the aryl hydrocarbon receptor decreases rifampicin-induced CYP3A4 expression in primary human hepatocytes and HepaRG. *Toxicology letters* 277, 1-8, doi:10.1016/j.toxlet.2017.05.029 (2017).
110. Williamson, B., Lorbeer, M., Mitchell, M. D., Brayman, T. G. & Riley, R. J. Evaluation of a novel PXR-knockout in HepaRG cells. *Pharmacology research & perspectives* 4, e00264, doi:10.1002/prp2.264 (2016).
111. Brauze, D. et al. Induction of expression of aryl hydrocarbon receptor-dependent genes in human HepaRG cell line modified by shRNA and treated with beta-naphthoflavone. *Molecular and cellular biochemistry* 425, 59-75, doi:10.1007/s11010-016-2862-3 (2017).
112. Fabian, M. A. et al. A small molecule-kinase interaction map for clinical kinase inhibitors. *Nat Biotechnol* 23, 329-336, doi: 10.1038/nbt1068 (2005).
113. Karaman, M. W. et al. A quantitative analysis of kinase inhibitor selectivity. Nat Biotechnol 26, 127-132, doi: 10.1038/nbt1358 (2008).

What is claimed is:

1. A pharmaceutical composition comprising a therapeutically effective amount of one or more of compounds of Formula (I) or pharmaceutically acceptable salts thereof, and a pharmaceutically acceptable carrier, wherein Formula (I) is represented as

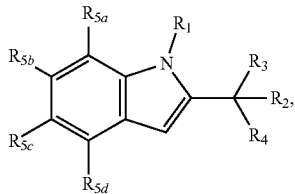
(I)

wherein $R_1$ is H, alkoxy, ethoxymethyl, or

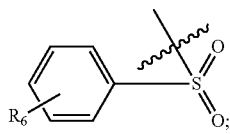

$R_2$ is H, 2-indolyl, 1-prop-1-ynyl, 3-prop-1-ynyl or 4-pyridyl;

$R_3$ is OH; O-alkyl or =O, provided that when $R_3$ is =O, $R_2$ void;

$R_4$ is

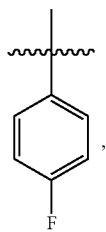

,

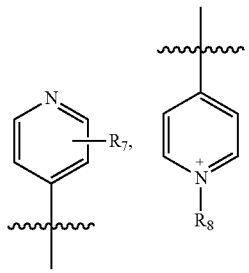 , 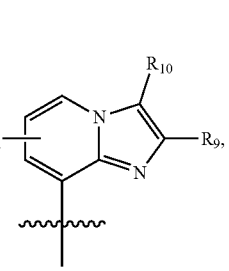 ,

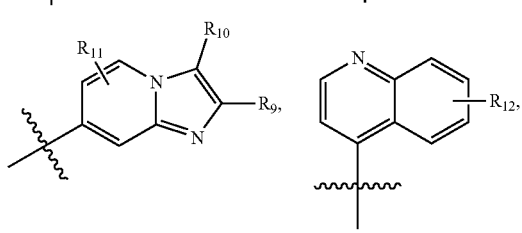

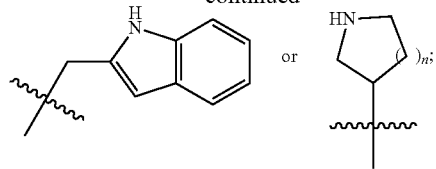

$R_{5a}$, $R_{5b}$, $R_{5c}$ and $R_{5d}$ are each independently hydrogen, halogen, alkyl, alkoxy, $NH_2$, NHR, $N(R)_2$, OH, phenyl, or phenyl substituted with one or more alkyl, halogen, OH or $NH_2$;

$R_6$ is H, halogen, alkyl, alkoxy, $NH_2$, NHR, $N(R)_2$, $CF_3$ or OH;

$R_7$ is H, halogen, alkyl, alkoxy, $NH_2$, NHR, $N(R)_2$ or $CF_3$;

$R_8$ is alkyl;

$R_9$, $R_{10}$ and $R_{11}$ are each independently H, halogen, alkyl, alkoxy, $NH_2$, NHR, $N(R)_2$, OH, phenyl, or phenyl substituted with one or more alkyl, halogen, OH or $NH_2$;

$R_{12}$ is H, halogen, alkyl, alkoxy, $NH_2$, NHR, $N(R)_2$, OH, phenyl, or phenyl substituted with one or more alkyl, halogen, OH or $NH_2$;

R is alkyl;

n is 1 or 2; and

~~~ represents the point of attachment to the scaffold, provided that when $R_1$ is $SO_2Ph$, $R_3$ is =O, and $R_{5a}$, $R_{5b}$, $R_{5c}$ and $R_{5d}$ are each hydrogen, $R_4$ is not

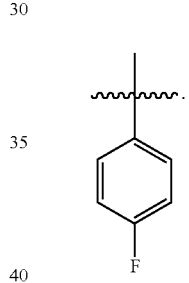.

2. The pharmaceutical composition of claim 1, wherein the one or more of compounds are selected from the group consisting of

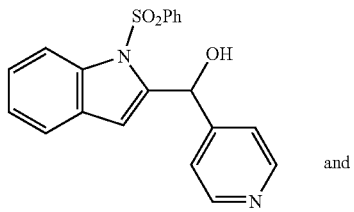

and

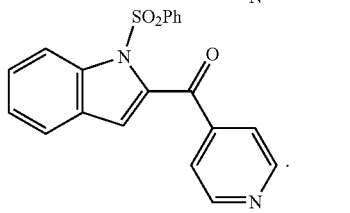.

3. A method of treating or preventing gut barrier dysfunction, an illness associated with gut barrier dysfunction, toxic or inflammatory injury to intestines, or leaky intestinal syndrome in a subject comprising administering to the subject one or more compounds of Formula (I) or pharmaceutically acceptable salts thereof in an amount effective to treat or prevent gut barrier dysfunction, an illness associated with gut barrier dysfunction, toxic or inflammatory injury to intestines, or leaky intestinal syndrome in a subject, wherein Formula (I) is represented as

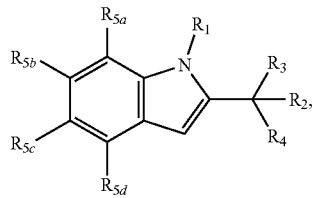

wherein
$R_1$ is H, alkoxy, ethoxymethyl, or

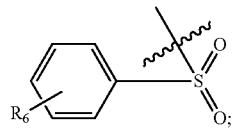

$R_2$ is H, 2-indolyl, 1-prop-1-ynyl, 3-prop-1-ynyl or 4-pyridyl;
$R_3$ is OH; O-alkyl or =O, provided that when $R_3$ is =O, $R_2$ void;
$R_4$ is

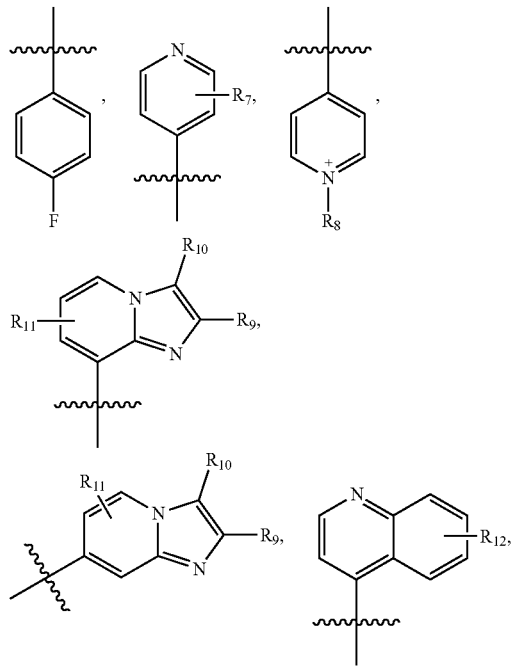

-continued

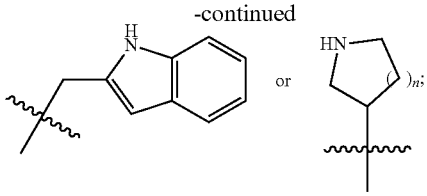

$R_{5a}$, $R_{5b}$, $R_{5c}$ and $R_{5d}$ are each independently hydrogen, halogen, alkyl, alkoxy, $NH_2$, NHR, $N(R)_2$, OH, phenyl, or phenyl substituted with one or more alkyl, halogen, OH or $NH_2$;
$R_6$ is H, halogen, alkyl, alkoxy, $NH_2$, NHR, $N(R)_2$, $CF_3$ or OH;
$R_7$ is H, halogen, alkyl, alkoxy, $NH_2$, NHR, $N(R)_2$ or $CF_3$;
$R_8$ is alkyl;
$R_9$, $R_{10}$ and $R_{11}$ are each independently H, halogen, alkyl, alkoxy, $NH_2$, NHR, $N(R)_2$, OH, phenyl, or phenyl substituted with one or more alkyl, halogen, OH or $NH_2$;
$R_{12}$ is H, halogen, alkyl, alkoxy, $NH_2$, NHR, $NHR_2$, OH, phenyl, or phenyl substituted with one or more alkyl, halogen, OH or $NH_2$;
R is alkyl;
n is 1 or 2; and
∿ represents the point of attachment to the scaffold.

4. The method of claim 3, wherein the subject has irritable bowel syndrome, inflammatory bowel disease, intestinal allergic syndrome or celiac sprue.

5. The method of claim 3, wherein the subject is at risk for developing gut barrier dysfunction, and/or an illness associated with gut barrier dysfunction, due to a toxin, a medication, poor diet, a parasite, an infection, dysbiosis, bacterial overgrowth, or long-term use of an antibiotic.

6. The method of claim 3, wherein the illnesses associated with gut barrier dysfunction is selected from the group consisting of inflammatory bowel disease, irritable bowel syndrome, fatty liver disease, colon cancer, cardiovascular disease, pulmonary disease and autoimmune disease.

7. The method of claim 3, wherein the one or more compounds are selected from the group consisting of

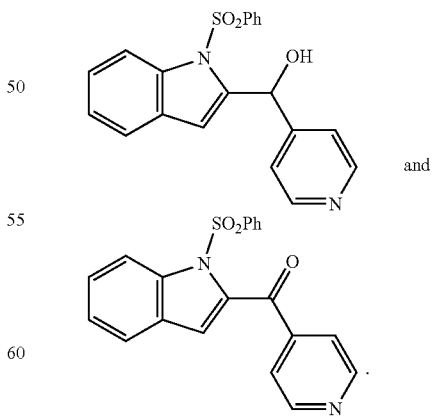

8. The method of claim 3, wherein the subject is a human.

9. The pharmaceutical composition of claim 1, wherein $R_1$ is H,

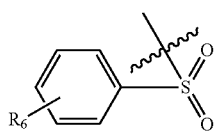

or ethoxymethyl, $R_2$ is H, 2-indolyl, 1-prop-1-ynyl, 3-prop-1-ynyl, or 4-pyridyl.

10. The pharmaceutical composition of claim 9, wherein $R_4$ is

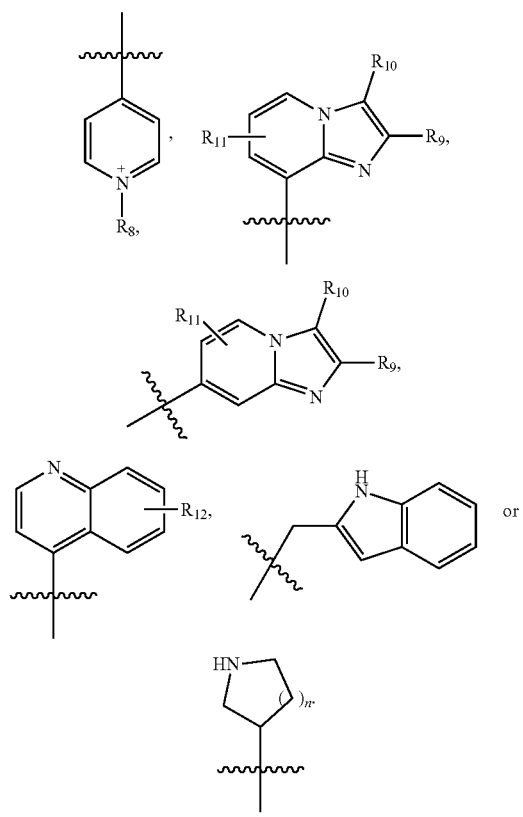

11. The pharmaceutical composition of claim 9, wherein $R_4$ is

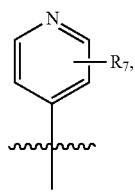

provided that (a) when $R_1$ is $SO_2Ph$, $R_3$ is OH, $R_7$ is H or halogen, and $R_{5a}$, $R_{5b}$, $R_{5c}$ and $R_{5d}$ are each hydrogen, $R_2$ is not H; and (b) when $R_1$ is $SO_2Ph$ or H, $R_3$ is =O, and $R_{5a}$, $R_{5b}$, $R_{5c}$ and $R_{5a}$ are each hydrogen, $R_7$ is not H.

12. The method of claim 3, wherein $R_1$ is H,

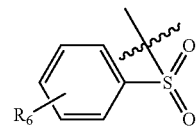

or ethoxymethyl, $R_2$ is H, 2-indolyl, 1-prop-1-ynyl, 3-prop-1-ynyl or 4-pyridyl.

13. The method of claim 3, wherein the one or more compounds are selected from the group consisting of

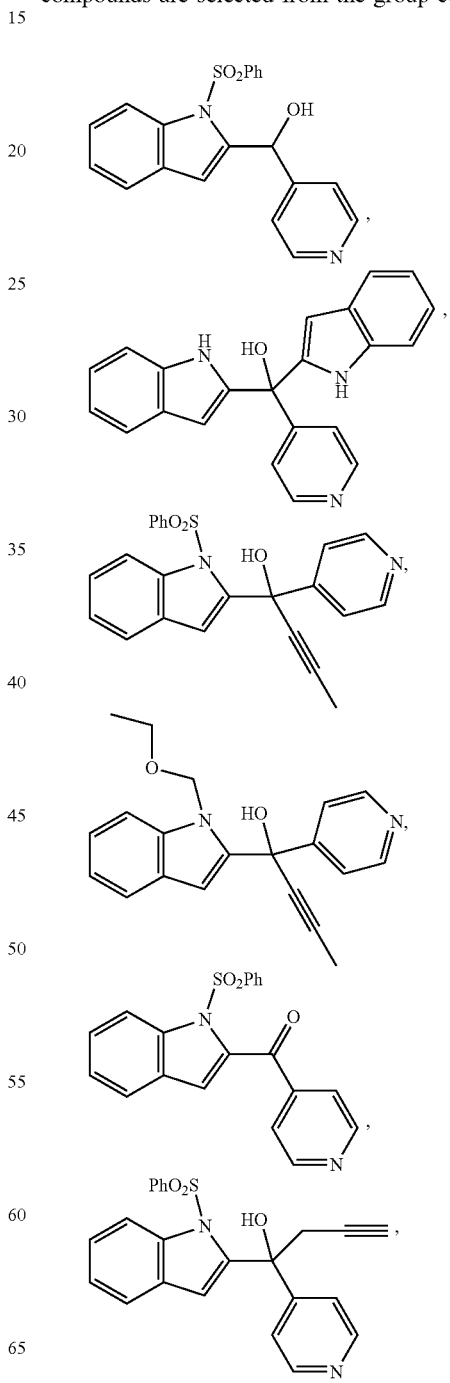

51
-continued
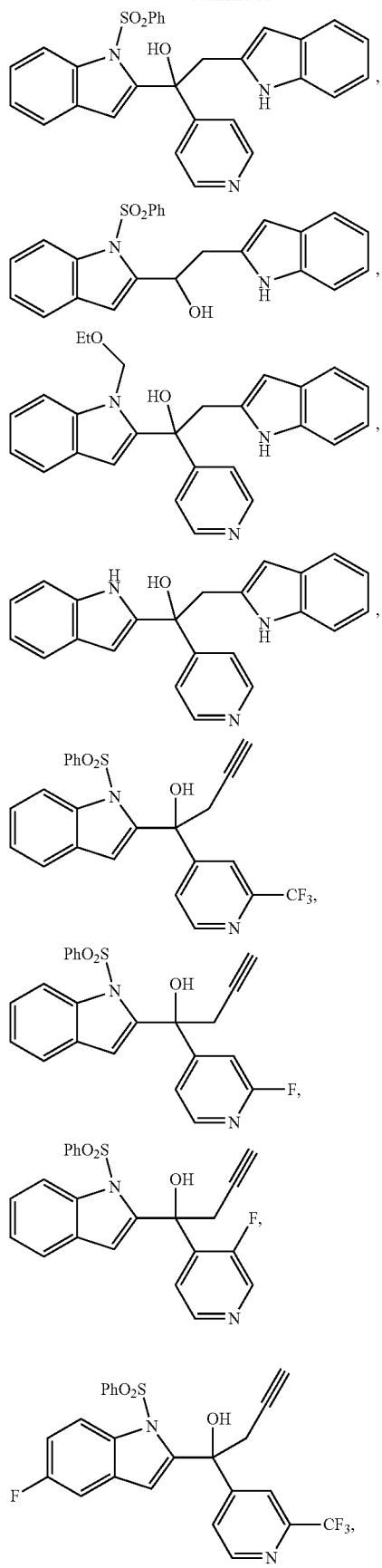
52
-continued
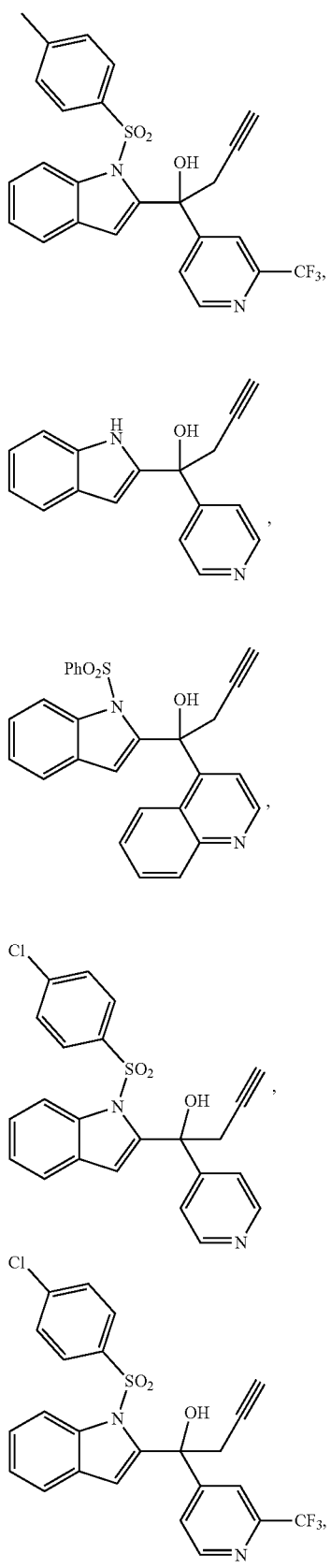

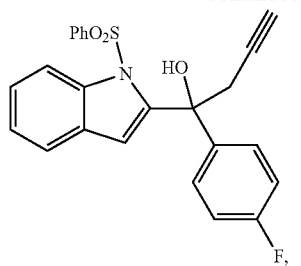
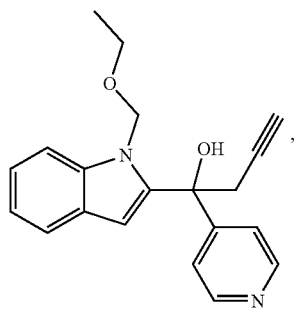
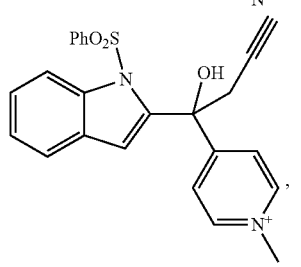
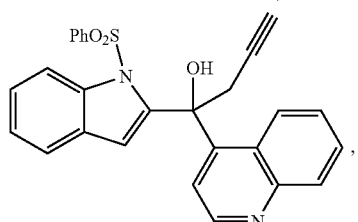
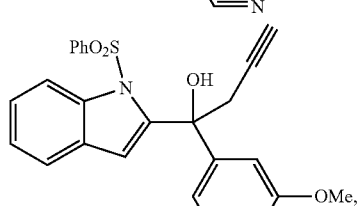
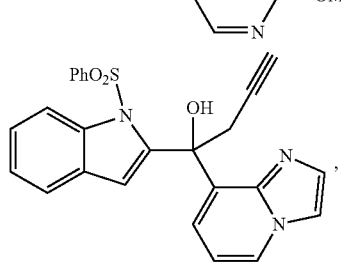
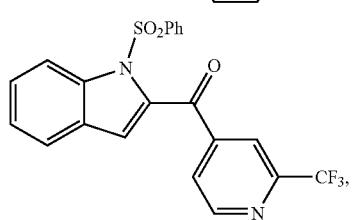
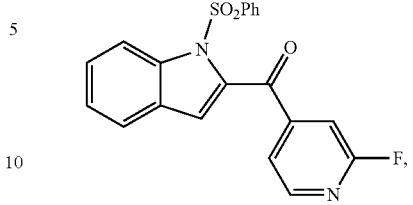
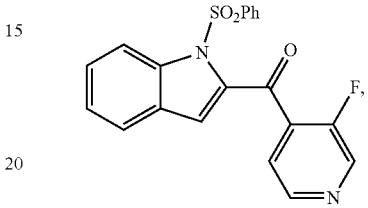
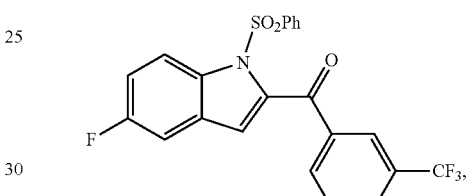
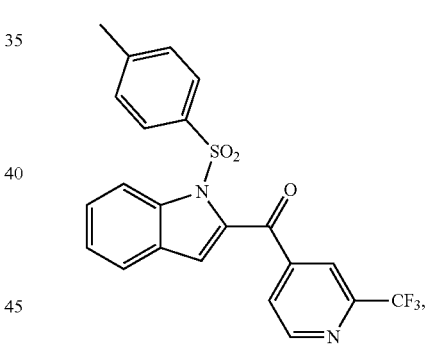
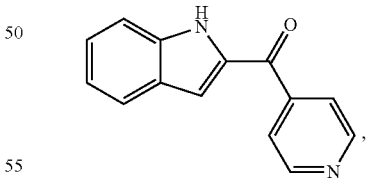
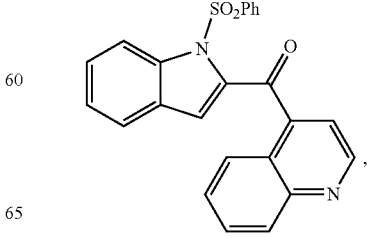

-continued
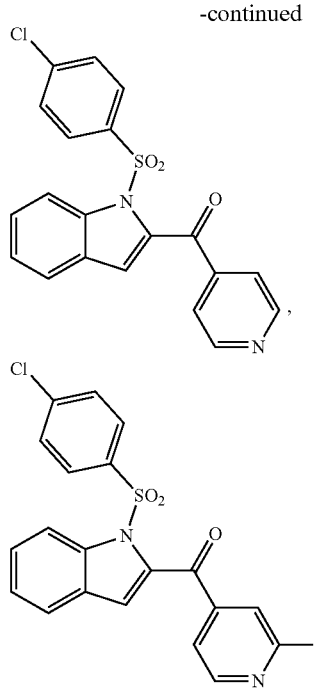
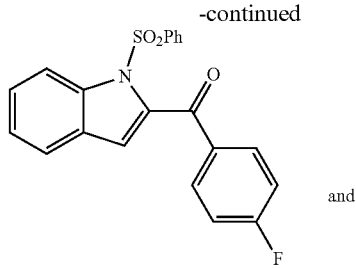
and
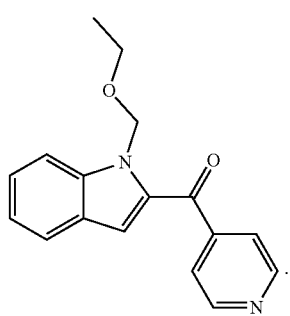
* * * * *